US011734257B2

(12) United States Patent
Haddon et al.

(10) Patent No.: US 11,734,257 B2
(45) Date of Patent: *Aug. 22, 2023

(54) VARIATION RECOGNITION BETWEEN HETEROGENEOUS COMPUTER SYSTEMS

(71) Applicant: eAffirm LLC, Austin, TX (US)

(72) Inventors: Brian Haddon, Austin, TX (US); Ryan Owen, Austin, TX (US)

(73) Assignee: eAffirm LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/467,401

(22) Filed: Sep. 6, 2021

(65) Prior Publication Data

US 2022/0004537 A1     Jan. 6, 2022

Related U.S. Application Data

(63) Continuation of application No. 15/927,080, filed on Mar. 20, 2018, now Pat. No. 11,113,263.

(51) Int. Cl.
*G06F 16/23* (2019.01)
*H04L 1/16* (2023.01)
(Continued)

(52) U.S. Cl.
CPC ......... *G06F 16/2365* (2019.01); *G06Q 30/04* (2013.01); *G16H 10/60* (2018.01);
(Continued)

(58) Field of Classification Search
None
See application file for complete search history.

(56) References Cited

U.S. PATENT DOCUMENTS

2002/0133504 A1* 9/2002 Vlahos .................. G06F 16/256
2005/0065987 A1* 3/2005 Telkowski ............ G06F 16/119
(Continued)

*Primary Examiner* — Eddy Cheung
(74) *Attorney, Agent, or Firm* — Michael G. Smith, Esq.

(57) ABSTRACT

In some implementations a computer-accessible medium includes a multimedia-document integration module that includes a heterogeneous distinction identifier between a first multimedia-document and a second multimedia-document and includes an integrator of the first multimedia-document and the second multimedia-document into an integrated multimedia-document, a data capture module that includes a data-extractor of the integrated multimedia-document, a query module that includes a query-generator encapsulated in a corresponding number of enquiry/inquiry transmissions, the enquiry/inquiry transmissions being short-message-service text-messages, a communication-subsystem that includes a transmitter of the enquiry/inquiry transmissions to an external device and receiver of an acknowledgement transmission or a negative-acknowledgement transmission from the external device, the acknowledgement/negative-acknowledgement transmission being a short-message-service text-message, and, a variance analytic module that includes a generator of quantitative variance from the acknowledgement/negative-acknowledgement transmission, the quantitative variance describing statistical variances and discrepancies within the first multimedia-document and within the second multimedia-document and between the first multimedia-document and the second multimedia-document.

2 Claims, 17 Drawing Sheets

(51) Int. Cl.
*G16H 10/60* (2018.01)
*G06Q 30/04* (2012.01)
*H04W 4/14* (2009.01)
*H04L 67/52* (2022.01)
*H04L 67/01* (2022.01)

(52) U.S. Cl.
CPC ............... *H04L 1/16* (2013.01); *H04L 67/52* (2022.05); *H04W 4/14* (2013.01); *H04L 67/01* (2022.05)

(56) References Cited

U.S. PATENT DOCUMENTS

| | | | | |
|---|---|---|---|---|
| 2005/0187797 | A1* | 8/2005 | Johnson | G16H 20/10 |
| | | | | 705/3 |
| 2006/0253413 | A1* | 11/2006 | Dihlmann | H04M 1/2757 |
| 2008/0172596 | A1* | 7/2008 | Weidner | G06F 16/93 |
| | | | | 715/201 |
| 2008/0177770 | A1* | 7/2008 | Friedlander | G06F 16/256 |
| 2009/0106374 | A1* | 4/2009 | Easwar | G06Q 10/107 |
| | | | | 455/466 |
| 2010/0016002 | A1* | 1/2010 | Konicek | H04W 4/14 |
| | | | | 455/466 |
| 2011/0307499 | A1* | 12/2011 | Elias | G06F 16/34 |
| | | | | 707/750 |
| 2012/0005252 | A1* | 1/2012 | Canessa | G06F 16/51 |
| | | | | 709/201 |

\* cited by examiner

VARIATION RECOGNITION BETWEEN HETEROGENEOUS COMPUTER SYSTEMS

RELATED APPLICATION

This application is a continuation of U.S. Ser. No. 15/927,080 filed on 20 Mar. 2018.

FIELD OF THE INVENTION

This disclosure relates generally to an architecture between computer systems, and more particularly to managing status and affirmation between heterogeneous computer systems.

BACKGROUND OF THE INVENTION

The organization of heterogeneous computer systems is extraordinarily confusing. The nature and description of the systems is difficult to ascertain by either a computer-implemented process or an animate entity. As a result, the process from one location to another can be convoluted, disorganized, corrupted by fraud, delayed, erroneous and sometimes the entire process is not completed.

BRIEF DESCRIPTION OF THE INVENTION

In one aspect, a computer-accessible medium includes a multimedia-document integration module that includes a heterogeneous distinction identifier between a first multimedia-document and a second multimedia-document and includes an integrator of the first multimedia-document and the second multimedia-document into an integrated multimedia-document, a data capture module that includes a data-extractor of the integrated multimedia-document, a query module that includes a query-generator encapsulated in a corresponding number of enquiry/inquiry transmissions, the enquiry/inquiry transmissions being short-message-service text-messages, a communication-subsystem that includes a transmitter of the enquiry/inquiry transmissions to an external device and receiver of an acknowledgement transmission or a negative-acknowledgement transmission from the external device, the acknowledgement/negative-acknowledgement transmission being a short-message-service text-message, and, a variance analytic module that includes a generator of quantitative variance from the acknowledgement/negative-acknowledgement transmission, the quantitative variance describing statistical variances and discrepancies within the first multimedia-document and within the second multimedia-document and between the first multimedia-document and the second multimedia-document.

DETAILED DESCRIPTION OF THE INVENTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into five sections. In the first section, a system level overview is described. In the second section, implementations of apparatus are described. In the third section, method implementations are described. In the fourth section, a conclusion of the detailed description is provided.

System Level Overview

Figure 1:
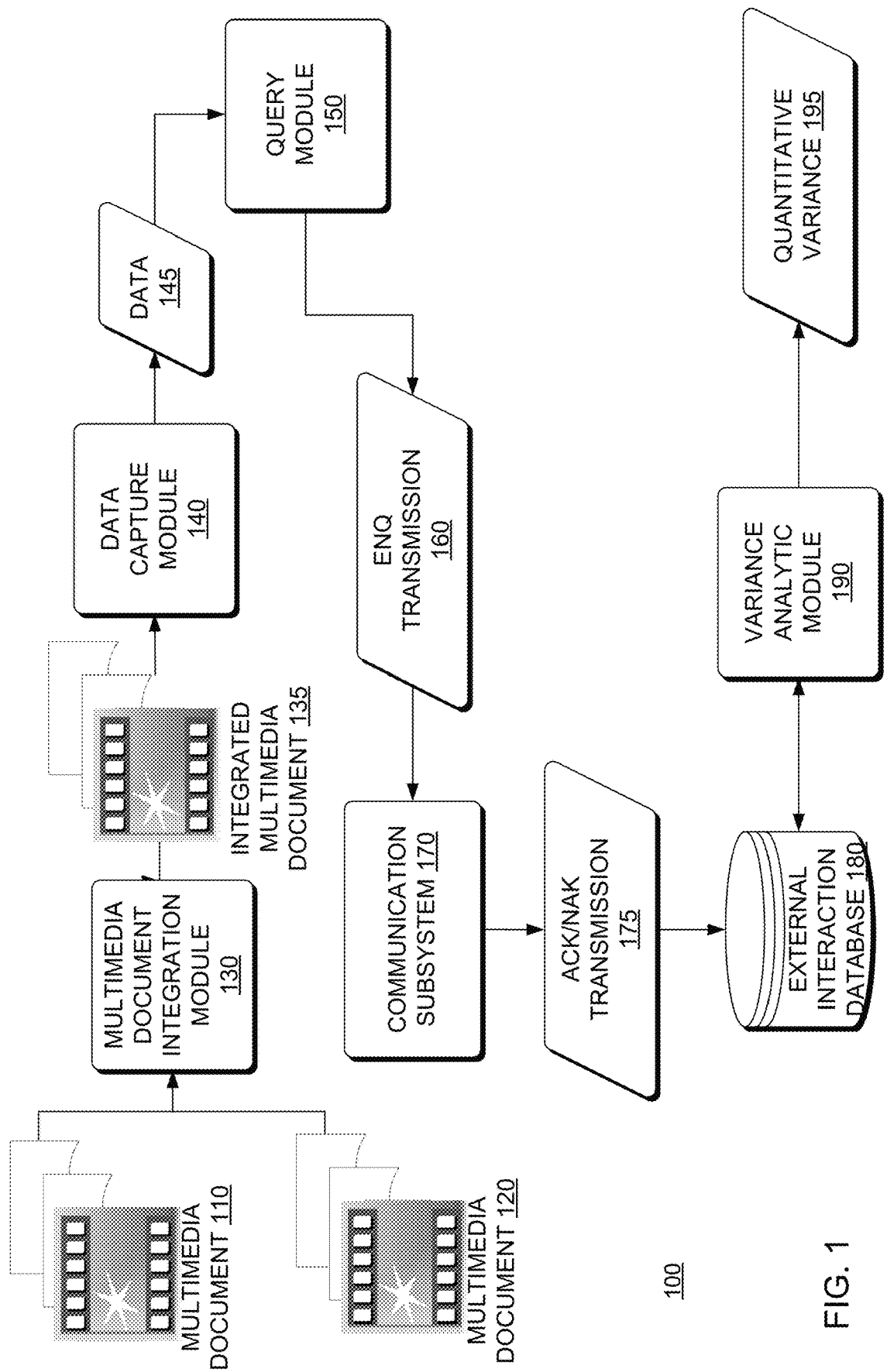
FIG. 1 is a block diagram of an overview of a multimedia document interchange variance detection system to exchange information in a predetermined architecture of multimedia object interchange, according to an implementation.

FIG. 1 is a block diagram of an overview of a multimedia document interchange variance detection system 100 to exchange information in a predetermined architecture of multimedia object interchange, according to an implementation.

The multimedia document interchange variance detection system 100 receives a multimedia document 110 and optionally another multimedia document 120 into a multimedia document integration module 130. The multimedia document integration module 130 includes a heterogeneous distinction identifier between the multimedia document 110 and the multimedia document 120. The multimedia document integration module 130 integrates the multimedia document 110 and the multimedia document 120, generating an integrated multimedia document 135. In some implementations, the multimedia document 110 and the multimedia document 120 are received from heterogeneous computer systems and have heterogeneous file formats. In some implementations, the multimedia document 110 has a heterogeneous internal organization to the multimedia document 120. The heterogeneous distinctions are identified before generating the integrated multimedia document 135.

The integrated multimedia document 135 is received by a data capture module 140 and extracts data 145 from the integrated multimedia device-independent document 135. A query module 150 receives the extracted data 145 from the data capture module 140 and generates one or more queries that are encapsulated in a corresponding number of ENQ (enquiry/inquiry) transmission(s) 160. The ENQ transmission(s) 160 are received by a communication subsystem 170, the communication subsystem 170 transmits the ENQ transmission(s) 160 to an external device (such as client device 204 as described in greater detail in FIG. 2) and the external device (e.g. client devices 204) responds with an ACK (acknowledgement) message or a NACK (negative [not] acknowledgement) transmission 175. In some implementations, the ENQ transmission 160 and the ACK/NACK transmission 175 are short-message-service (SMS) text messages, as defined in RFC 1568, RFC 1645 and RFC 1861 published by the Internet Engineering Task Force (https://www.ietf.org). In some implementations, the ACK message is a single character message indicating acknowledgement of the corresponding ENQ transmission 160. In some implementations, a NACK transmission is not implemented, but instead the absence of an ACK transmission from the external device is interpreted by the communication subsystem 170 as a NACK transmission. The ACK/NACK transmission 175 is stored in an interaction database 210. A variance analytic module 190 that verifies and cross-references active healthcare providers in the extracted data in reference to the healthcare provider table and the superbill table in the external interaction database and that verifies and cross references patient identification in the superbill table and the extracted data, and that retrieves the ACK/NACK transmission 175 from the interaction database 210 and the variance analytic module 190 generates a quantitative variance 195 from the retrieved ACK/NACK transmission 175. The quantitative variance 195 describes statistical variances and discrepancies within the multimedia document 110 and within the multimedia document 120 and between the multimedia document 110 and the multimedia document 120.

Apparatus Implementation

Figure 2:
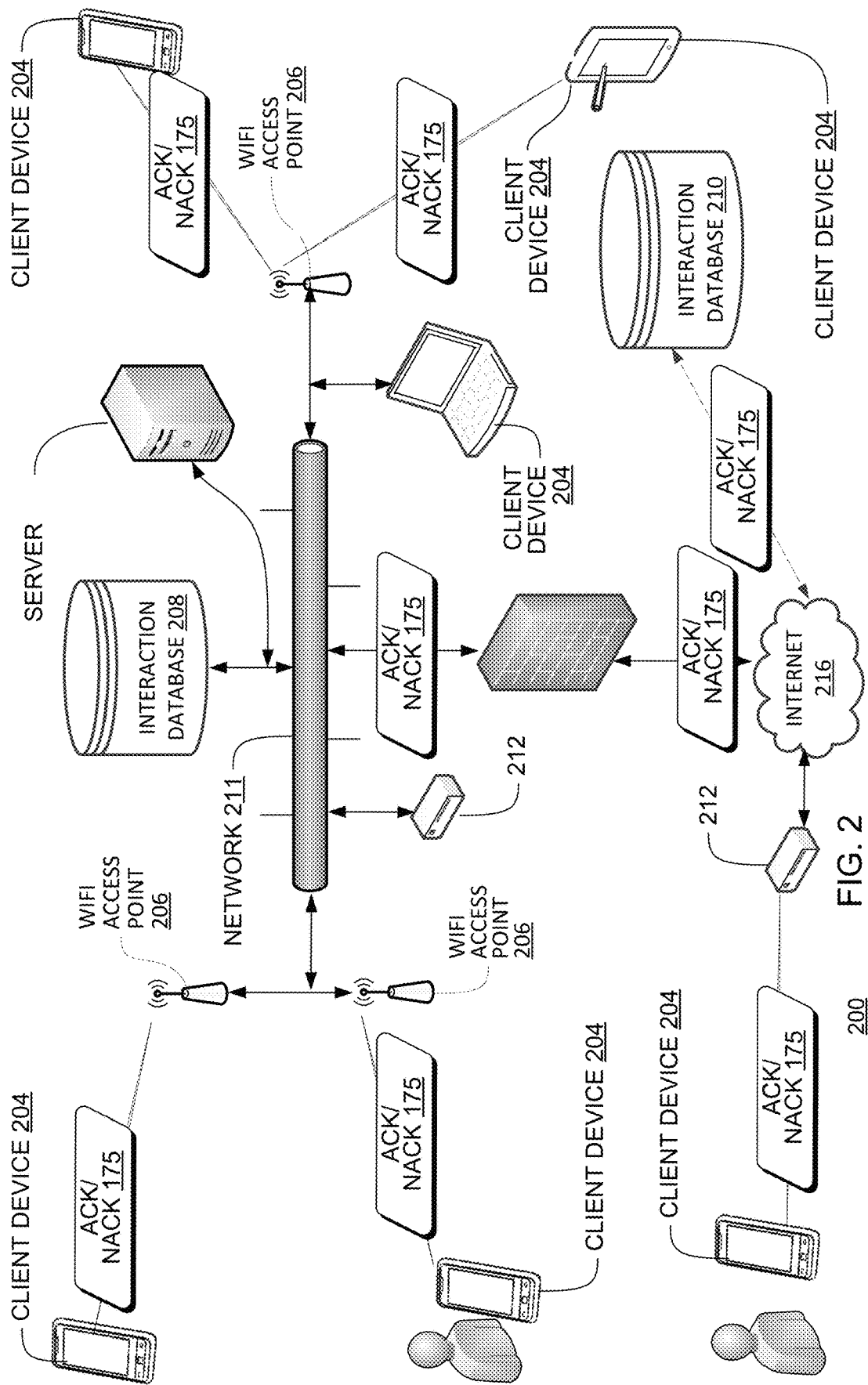
FIG. 2 is a block diagram of an implementation of an apparatus of a variance detection system, according to an implementation.

FIG. 2 is a block diagram of an implementation of an apparatus of a variance detection system 200, according to an implementation.

FIG. 2 shows high level components of the variance detection system 200 that includes a server 202. The server 202 transfers the ENQ transmission 160 to the client device 204 and transfers the ACK/NACK transmission 175 from client devices 204. Examples of client device 204 include the hand-held device 400, the computing system 500 in FIG. 5 and the tablet computer 800.

The variance detection system 200 includes two important aspects:

1. A server 202 to control the flow of quantitative metrics from client device 204 to one or more interaction databases 210 and to manage local client devices 204.

2. To transfer of quantitative metrics in an ACK/NACK transmission 175, anonymous, and other information to interaction database 210.

In some implementations, some of the client devices 204 are connected to the variance detection system 200 via a WIFI connection to a Wi-Fi access point 206. The server 202 controls and manages the flow of quantitative metrics to an interaction database 208 and/or an interaction database 210 and provides management services to client devices 204.

The server 202 provides an interface to:
Location specific service components, per healthcare provider, for verification of active operator, and if necessary, patient identifications.
A cloud based data repository (interaction database 210) of one or more client devices 204, for the purpose of storing all measurement records in an anonymous manner for analysis. A setup, management and reporting mechanism also provided.

The server 202 accepts communications from client device 204 to:
Data format conversion and transferring patient measurement records to interaction database 210.
Manage the firmware and configuration settings of the client devices 204.
Determine current health and status of the client devices 204.
Support device level protocol for communications, TCP/IP, of that supports the following core features:
Authentication of connected device and server 202
Transfer of patient measurement records to server 202 with acknowledgement and acceptance by the server 202 or interaction acceptance.
Support for dynamic update of configuration information and recovery of health and status of the client devices 204.
Support for firmware update mechanism of firmware of client devices 204.

The variance detection system 200 provides high availability, 24/7/365, with 99.99% availability.

The variance detection system 200 provides a scalable server system to meet operational demands in healthcare provider operational environments for one or both of the following deployable cases:

1. A local network 211 at an operational site in which the server 202 provides all features and functions in a defined operational network 211 to communicate to any number of client devices 204.

2. Interaction database 210 in which the server 202 communicates to client devices 204.

Figure 9:
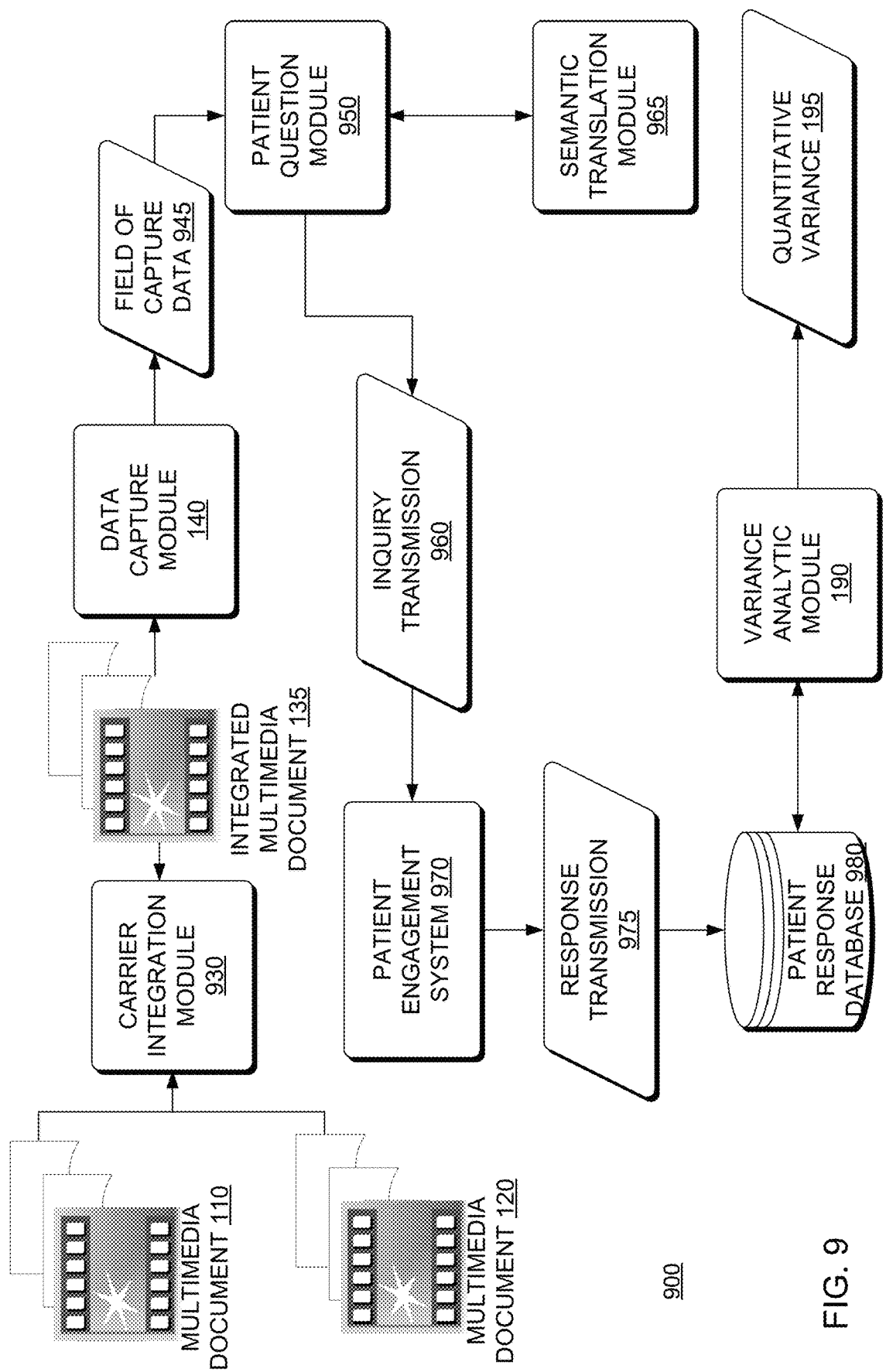
FIG. 9 is a block diagram of a multimedia document interchange variance detection system to exchange information in a predetermined architecture of multimedia object interchange, according to an implementation.

The server 202 provides a central management system for the client devices 204 and includes the multimedia document interchange variance detection system 100 in FIG. 1 and multimedia document interchange variance detection system 900 in FIG. 9.

The server 202 provides extendable features, via software updates, to allow for the addition of enhanced features without the need for additional hardware component installation at the installation site. The server 202 provides a device level commission mechanism and interface for the initial setup, configuration and test of client device 204 on the network 211.

Coverage of the variance detection system 200 of a healthcare provider can include various locations, wards, ER rooms, offices, Dr's Offices etc. or anywhere where variance detection in patient billing is required.

The client device 204 can communicate with a third party bridge 212 to provide access to data storage services, interaction systems, hand-held devices cloud storage system etc.

Networking setup, configuration, performance characteristics etc. are also determined and carried out by the third party bridge 212 or another third party, for the operational environments. The hand-held devices can support the network protocols for communication with the third party bridge 212 devices.

Some implementations of FIG. 2 the server 202 is a remote cloud based bridge. The remote cloud based bridge and the interaction database 208 are operably coupled to the network 211 via the Internet 216.

Figure 3:
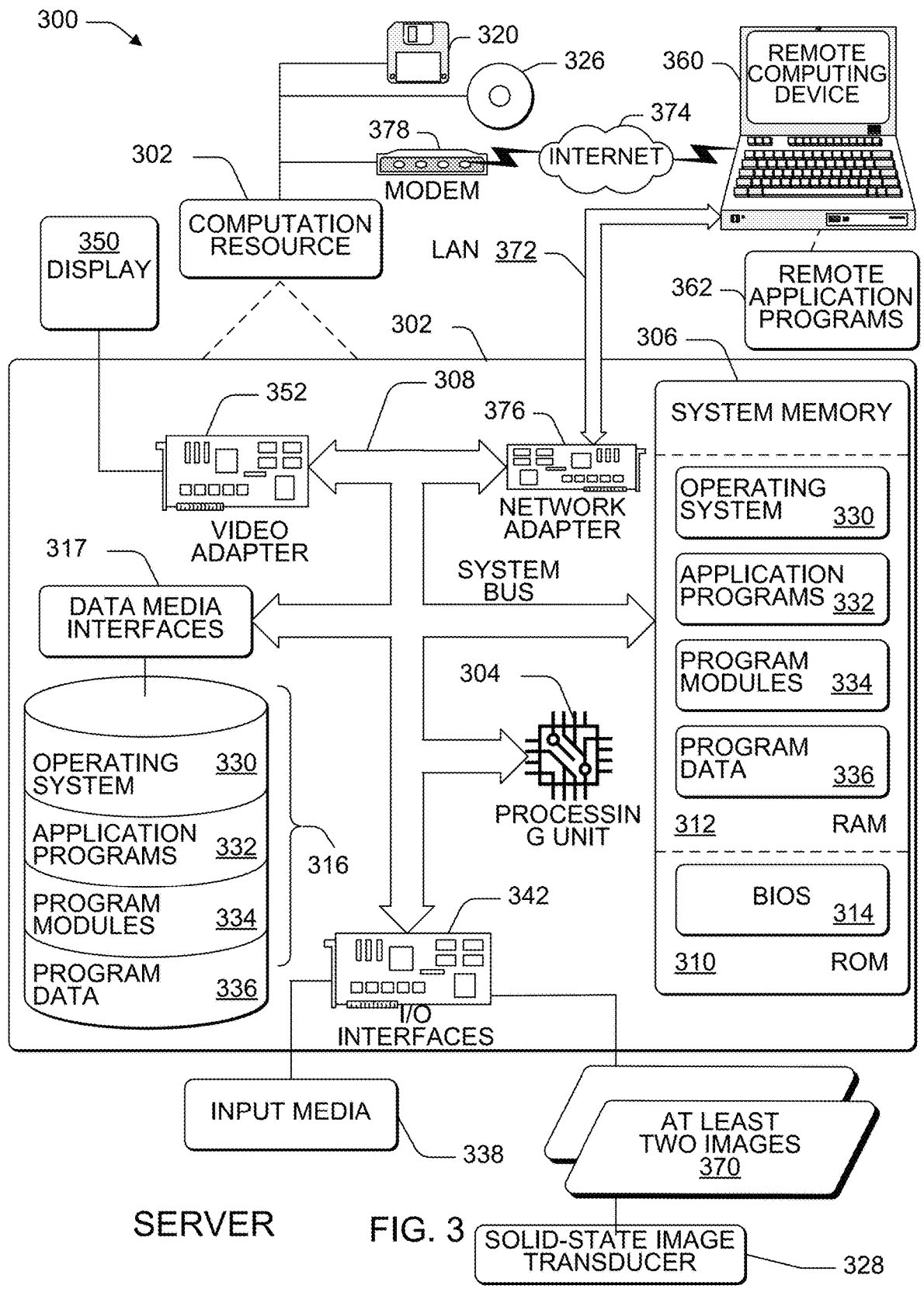
FIG. 3 is a block diagram of a variance detection server, according to an implementation.

FIG. 3 is a block diagram of a variance detection server 300, according to an implementation. The description of FIG. 3 provides an overview of computer hardware and a suitable computing environment in conjunction with which some implementations can be implemented. Implementations are described in terms of a computer executing computer-executable instructions. However, some implementations can be implemented entirely in computer hardware in which the computer-executable instructions are implemented in read-only memory. Some implementations can also be implemented in client/server computing environments where remote devices that perform tasks are linked through a communications network. Program modules can be located in both local and remote memory storage devices in a distributed computing environment.

FIG. 3 illustrates an example of a variance detection server 300 useful in the context of the environment of FIG. 2, in accordance with an implementation. Variance detection server 300 is one example of server 202 in FIG. 2. The variance detection server 300 includes a computation resource 302 capable of implementing the processes described herein. It will be appreciated that other devices can alternatively be used that include more modules, or fewer modules, than those illustrated in FIG. 3.

The illustrated operating variance detection server 300 is only one example of a suitable operating environment, and the example described with reference to FIG. 3 is not intended to suggest any limitation as to the scope of use or functionality of the implementations of this disclosure. Other well-known computing systems, environments, and/or configurations can be suitable for implementation and/or application of the subject matter disclosed herein.

The computation resource 302 includes one or more processors or processing units 304, a system memory 306, and a system bus 308 that couples various system modules including the system memory 306 to processing unit 304 and other elements in the variance detection server 300. The system bus 308 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols.

The system memory 306 includes nonvolatile read-only memory (ROM) 310 and random access memory (RAM) 312, which can or can not include volatile memory elements. A basic input/output system (BIOS) 314, containing the elementary routines that help to transfer information between elements within computation resource 302 and with external items, typically invoked into operating memory during start-up, is stored in ROM 310.

The computation resource 302 further can include a non-volatile read/write memory 316, represented in FIG. 3 as a hard disk drive, coupled to system bus 308 via a data media interface 317 (e.g., a SCSI, ATA, or other type of interface); a magnetic disk drive (not shown) for reading from, and/or writing to, a removable magnetic disk 320 and an optical disk drive (not shown) for reading from, and/or writing to, a removable optical disk 326 such as a CD, DVD, or other optical media.

The non-volatile read/write memory 316 and associated computer-readable media provide nonvolatile storage of computer-readable instructions, data structures, program modules and other data for the computation resource 302. Although the variance detection server 300 is described herein as employing a non-volatile read/write memory 316, a removable magnetic disk 320 and a removable optical disk 326, it will be appreciated by those skilled in the art that other types of computer-readable media which can store data that is accessible by a computer, such as magnetic cassettes, FLASH memory cards, random access memories (RAMs), read only memories (ROM), and the like, can also be used in the exemplary operating environment.

A number of program modules can be stored via the non-volatile read/write memory 316, removable magnetic disk 320, removable optical disk 326, ROM 310, or RAM 312, including an operating system 330, one or more application programs 332, program modules 334 and program data 336. Examples of computer operating systems conventionally employed include the NUCLEUS® operating system, the LINUX® operating system, and others, for example, providing capability for supporting application programs 332 using, for example, code modules written in the C++® computer programming language. The application programs 332 and/or the program modules 334 include a multimedia document integration module 130 that integrates documents from a query module 150 that generates inquiries and responses are received from a variance analytic module 190 that generates the quantitative variance 195 that is displayed by display 350 or transmitted or enunciated by speaker or stored in memory 306.

A user can enter commands and information into computation resource 302 through input devices such as input media 338 (e.g., keyboard/keypad, tactile input or pointing device, mouse, foot-operated switching apparatus, joystick, touchscreen or touchpad, microphone, antenna etc.). Such input media 338 are coupled to the processing unit 304 through a conventional input/output interface 342 that is, in turn, coupled to the system bus 308. Display 350 or other type of display device is also coupled to the system bus 308 via an interface, such as a video adapter 352. Some implementations of the variance detection server 300 include a solid-state image transducer 328 that is operably coupled to the processing unit 304 and is operable to provide two or more images 370 to the multimedia document integration module 130 in the application programs 332 and/or the program modules 334.

The computation resource 302 can include capability for operating in a networked environment using logical connections to one or more remote computers, such as a remote computer 360. The remote computer 360 can be a personal computer, a server, a router, a network PC, a peer device or other common network node, and typically includes many or all of the elements described above relative to the computation resource 302. In a networked environment, program modules depicted relative to the computation resource 302, or portions thereof, can be stored in a remote memory storage device such as can be associated with the remote computer 360. By way of example, remote application programs 362 reside on a memory device of the remote computer 360. The logical connections represented in FIG. 3 can include interface capabilities, a storage area network (SAN, not illustrated in FIG. 3), local area network (LAN) 372 and/or a wide area network (WAN) 374, but can also include other networks.

Such networking environments are commonplace in modern computer systems, and in association with intranets and the Internet. In certain implementations, the computation resource 302 executes an Internet Web browser program (which can optionally be integrated into the operating system 330), such as the "Internet Explorer®" Web browser manufactured and distributed by the Microsoft Corporation of Redmond, Wash.

When used in a LAN-coupled environment, the computation resource 302 communicates with or through the local area network 372 via a network interface or adapter 376 and typically includes interfaces, such as a modem 378, or other apparatus, for establishing communications with or through the WAN 374, such as the Internet. The modem 378, which can be internal or external, is coupled to the system bus 308 via a serial port interface.

In a networked environment, program modules depicted relative to the computation resource 302, or portions thereof, can be stored in remote memory apparatus. It will be appreciated that the network connections shown are exemplary, and other means of establishing a communications link between various computer systems and elements can be used.

A user of a computer can operate in a networked environment using logical connections to one or more remote computers, such as a remote computer 360, which can be a personal computer, a server, a router, a network PC, a peer device or other common network node. Typically, a remote computer 360 includes many or all of the elements described above relative to the variance detection server 300 of FIG. 3.

The computation resource 302 typically includes at least some form of computer-readable media. Computer-readable media can be any available media that can be accessed by the computation resource 302. By way of example, and not limitation, computer-readable media can comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computation resource 302.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media include wired media, such as wired network or direct-wired connections, and wireless media, such as acoustic, RF, infrared and other wireless media. The scope of the term computer-readable media includes combinations of any of the above.

Figure 4:
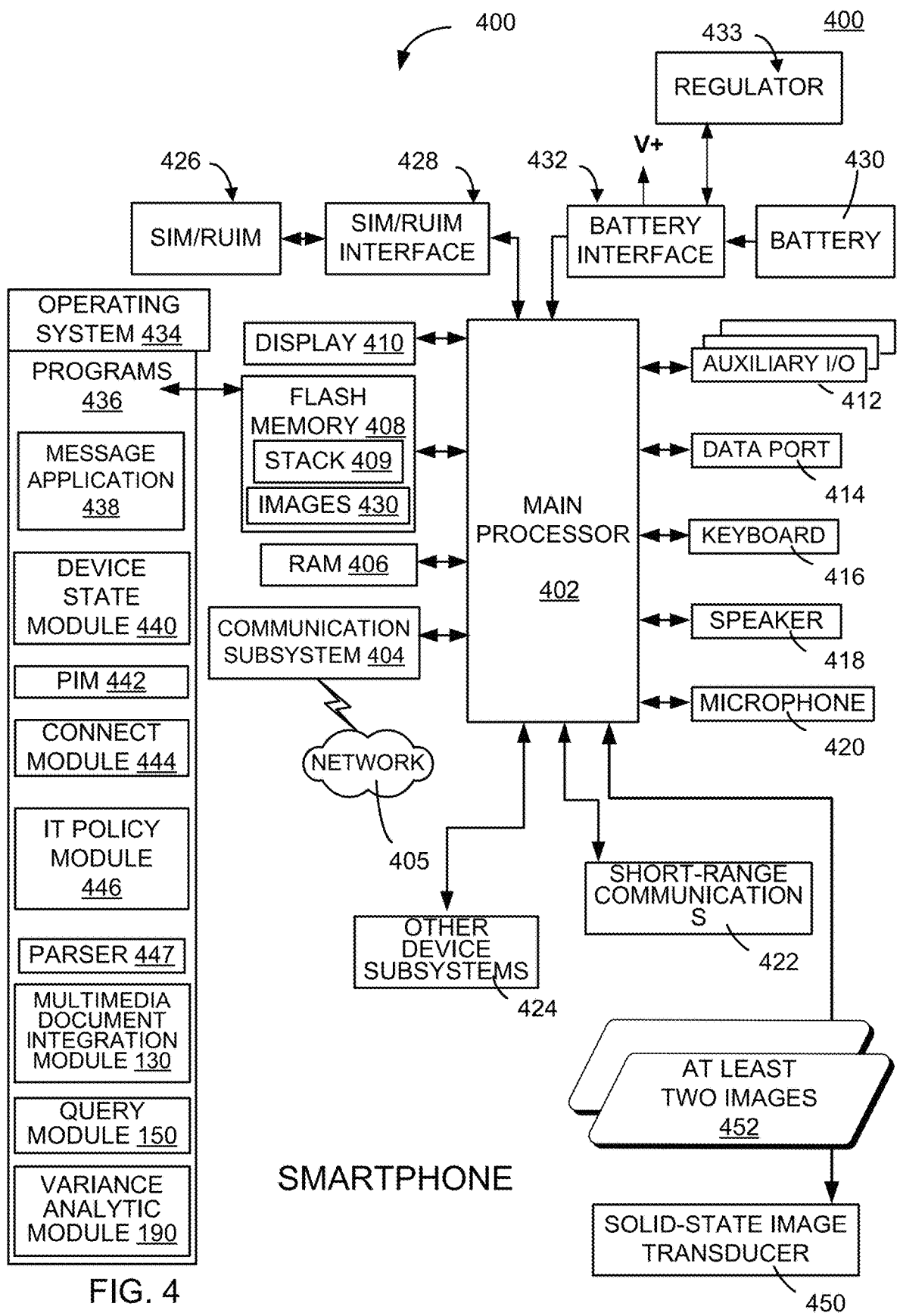
FIG. 4 is a block diagram of a hand-held device, according to an implementation.

FIG. 4 is a block diagram of a hand-held device 400, according to an implementation. The hand-held device 400 may also have the capability to allow voice communication. Depending on the functionality provided by the hand-held device 400, the hand-held device 400 may be referred to as a data messaging device, a two-way pager, a smartphone with data messaging capabilities, a wireless Internet appliance, or a data communication device (with or without telephony capabilities).

The hand-held device 400 includes a number of modules such as a main processor 402 that controls the overall operation of the hand-held device 400. Communication functions, including data and voice communications, are performed through a communication subsystem 404. The communication subsystem 404 receives messages from and sends messages to wireless networks 405. In other implementations of the hand-held device 400, the communication subsystem 404 can be configured in accordance with the Global System for Mobile Communication (GSM), General Packet Radio Services (GPRS), Enhanced Data GSM Environment (EDGE), Universal Mobile Telecommunications Service (UMTS), data-centric wireless networks, voice-centric wireless networks, and dual-mode networks that can support both voice and data communications over the same physical base stations. Combined dual-mode networks include, but are not limited to, Code Division Multiple Access (CDMA) or CDMA2000 networks, GSM/GPRS networks (as mentioned above), and future third-generation (3G) networks like EDGE and UMTS. Some other examples of data-centric networks include Mobitex™ and DataTAC™ network communication systems. Examples of other voice-centric data networks include Personal Communication Systems (PCS) networks like GSM and Time Division Multiple Access (TDMA) systems.

The wireless link connecting the communication subsystem 404 with the wireless network 405 represents one or more different Radio Frequency (RF) channels. With newer network protocols, these channels are capable of supporting both circuit switched voice communications and packet switched data communications.

The main processor 402 also interacts with additional subsystems such as a Random Access Memory (RAM) 406, a flash memory 408, a display 410, an auxiliary input/output (I/O) subsystem 412, a data port 414, a keyboard 416, a speaker 418, a microphone 420, short-range communications subsystem 422 and other device subsystems 424. In some implementations, the flash memory 408 includes a hybrid femtocell/Wi-Fi protocol stack 409. The hybrid femtocell/Wi-Fi protocol stack 409 supports authentication and authorization between the hand-held device 400 into a shared Wi-Fi network and both a 3G and 4G mobile networks.

Some of the subsystems of the hand-held device 400 perform communication-related functions, whereas other subsystems may provide "resident" or on-device functions. By way of example, the display 410 and the keyboard 416 may be used for both communication-related functions, such as entering a text message for transmission over the wireless network 405, and device-resident functions such as a calculator or task list.

The hand-held device 400 can transmit and receive communication signals over the wireless network 405 after required network registration or activation procedures have been completed. Network access is associated with a subscriber or user of the hand-held device 400. To identify a subscriber, the hand-held device 400 requires a SIM card/RUIM 426 (i.e. Subscriber Identity Module or a Removable User Identity Module) to be inserted into a SIM/RUIM interface 428 in order to communicate with a network. The SIM card/RUIM or 426 is one type of a conventional "smart card" that can be used to identify a subscriber of the hand-held device 400 and to personalize the hand-held device 400, among other things. Without the SIM card/RUIM 426, the hand-held device 400 is not fully operational for communication with the wireless network 405. By inserting the SIM card/RUIM 426 into the SIM/RUIM interface 428, a subscriber can access all subscribed services. Services may include: web browsing and messaging such as e-mail, voice mail, Short Message Service (SMS), and Multimedia Messaging Services (MMS). More advanced services may include: point of sale, field service and sales force automation. The SIM card/RUIM 426 includes a processor and memory for storing information. Once the SIM card/RUIM 426 is inserted into the SIM/RUIM interface 428, the SIM is coupled to the main processor 402. In order to identify the subscriber, the SIM card/RUIM 426 can include some user parameters such as an International Mobile Subscriber Identity (IMSI). An advantage of using the SIM card/RUIM 426 is that a subscriber is not necessarily bound by any single physical mobile device. The SIM card/RUIM 426 may store additional subscriber information for the hand-held device 400 as well, including datebook (or calendar) information and recent call information. Alternatively, user identification information can also be programmed into the flash memory 408.

The hand-held device 400 is a battery-powered device and includes a battery interface 432 for receiving one or more batteries 430. In one or more implementations, the battery 430 can be a smart battery with an embedded microprocessor. The battery interface 432 is coupled to a regulator 433, which assists the battery 430 in providing power V+ to the hand-held device 400. Although current technology makes use of a battery, future technologies such as micro fuel cells may provide the power to the hand-held device 400.

The hand-held device 400 also includes an operating system 434 and modules 436 to 447 which are described in more detail below. The operating system 434 and the modules 436 to 447 that are executed by the main processor 402 are typically stored in a persistent nonvolatile medium such as the flash memory 408, which may alternatively be a read-only memory (ROM) or similar storage element (not shown). Those skilled in the art will appreciate that portions of the operating system 434 and the modules 436 to 447, such as specific device applications, or parts thereof, may be temporarily loaded into a volatile store such as the RAM 406. Other modules can also be included.

The subset of modules 436 to 447 that control basic device operations, including data and voice communication applications, will normally be installed on the hand-held device 400 during its manufacture. Other modules include a message application 438 that can be any suitable module that allows a user of the hand-held device 400 to transmit and receive electronic messages. Various alternatives exist for the message application 438 as is well known to those skilled in the art. Messages that have been sent or received by the user are typically stored in the flash memory 408 of the hand-held device 400 or some other suitable storage element in the hand-held device 400. In one or more implementations, some of the sent and received messages may be stored remotely from the hand-held device 400 such as in a data store of an associated host system with which the hand-held device 400 communicates.

The modules can further include a device state module 440, a Personal Information Manager (PIM) 442, and other suitable modules (not shown). The device state module 440 provides persistence, i.e. the device state module 440 ensures that important device data is stored in persistent memory, such as the flash memory 408, so that the data is not lost when the hand-held device 400 is turned off or loses power.

The PIM 442 includes functionality for organizing and managing data items of interest to the user, such as, but not limited to, e-mail, contacts, calendar events, voice mails, appointments, and task items. A PIM application has an ability to transmit and receive data items via the wireless network 405. PIM data items may be seamlessly integrated, synchronized, and updated via the wireless network 405 with the hand-held device 400 subscriber's corresponding data items stored and/or associated with a host computer system. This functionality creates a mirrored host computer on the hand-held device 400 with respect to such items. This can be particularly advantageous when the host computer system is the hand-held device 400 subscriber's office computer system.

The hand-held device 400 also includes a connect module 444, and an IT policy module 446. The connect module 444 implements the communication protocols that are required for the hand-held device 400 to communicate with the wireless infrastructure and any host system, such as an enterprise system, with which the hand-held device 400 is authorized to interface. Examples of a wireless infrastructure and an enterprise system are given in FIGS. 4 and 5, which are described in more detail below.

The connect module 444 includes a set of APIs that can be integrated with the hand-held device 400 to allow the hand-held device 400 to use any number of services associated with the enterprise system. The connect module 444 allows the hand-held device 400 to establish an end-to-end secure, authenticated communication pipe with the host system. A subset of applications for which access is provided by the connect module 444 can be used to pass IT policy commands from the host system to the hand-held device 400. This can be done in a wireless or wired manner. These instructions can then be passed to the IT policy module 446 to modify the configuration of the hand-held device 400. Alternatively, in some cases, the IT policy update can also be done over a wired connection.

The IT policy module 446 receives IT policy data that encodes the IT policy. The IT policy module 446 then ensures that the IT policy data is authenticated by the hand-held device 400. The IT policy data can then be stored in the RAM 406 in its native form. After the IT policy data is stored, a global notification can be sent by the IT policy module 446 to all of the applications residing on the hand-held device 400. Applications for which the IT policy may be applicable then respond by reading the IT policy data to look for IT policy rules that are applicable.

The IT policy module 446 can include a parser 447, which can be used by the applications to read the IT policy rules. In some cases, another module or application can provide the parser. Grouped IT policy rules, described in more detail below, are retrieved as byte streams, which are then sent (recursively) into the parser to determine the values of each IT policy rule defined within the grouped IT policy rule. In one or more implementations, the IT policy module 446 can determine which applications are affected by the IT policy data and transmit a notification to only those applications. In either of these cases, for applications that are not being executed by the main processor 402 at the time of the notification, the applications can call the parser or the IT policy module 446 when the applications are executed to determine if there are any relevant IT policy rules in the newly received IT policy data.

All applications that support rules in the IT Policy are coded to know the type of data to expect. For example, the value that is set for the "WEP User Name" IT policy rule is known to be a string; therefore the value in the IT policy data that corresponds to this rule is interpreted as a string. As another example, the setting for the "Set Maximum Password Attempts" IT policy rule is known to be an integer, and therefore the value in the IT policy data that corresponds to this rule is interpreted as such.

After the IT policy rules have been applied to the applicable applications or configuration files, the IT policy module 446 sends an acknowledgement back to the host system to indicate that the IT policy data was received and successfully applied.

The modules 436 can also include a query module 150 and a variance analytic module 190. The multimedia document integration module 130 integrates documents from which the query module generates inquiries and responses are received from which the variance analytic module 190 generates the quantitative variance 195 that is displayed by display 410 or transmitted by communication subsystem 404 or short-range communications subsystem 422, enunciated by speaker 418 or stored by flash memory 408. Some implementations of the hand-held device 400 include a solid-state image transducer 450 that is operably coupled to the microprocessor 402 and is operable to provide two or more images 452 to the multimedia document integration module 130.

Other types of modules can also be installed on the hand-held device 400. These modules can be third party modules, which are added after the manufacture of the hand-held device 400. Examples of third party applications include games, calculators, utilities, etc.

The additional applications can be loaded onto the hand-held device 400 through of the wireless network 405, the auxiliary I/O subsystem 412, the data port 414, the short-range communications subsystem 422, or any other suitable device subsystem 424. This flexibility in application installation increases the functionality of the hand-held device 400 and may provide enhanced on-device functions, communication-related functions, or both. For example, secure communication applications may enable electronic commerce functions and other such financial transactions to be performed using the hand-held device 400.

The data port 414 enables a subscriber to set preferences through an external device or module and extends the capabilities of the hand-held device 400 by providing for information or module downloads to the hand-held device 400 other than through a wireless communication network. The alternate download path may, for example, be used to load an encryption key onto the hand-held device 400 through a direct and thus reliable and trusted connection to provide secure device communication.

The data port 414 can be any suitable port that enables data communication between the hand-held device 400 and another computing device. The data port 414 can be a serial or a parallel port. In some instances, the data port 414 can be a USB port that includes data lines for data transfer and a supply line that can provide a charging current to charge the battery 430 of the hand-held device 400.

The short-range communications subsystem 422 provides for communication between the hand-held device 400 and different systems or devices, without the use of the wireless network 405. For example, the short-range communications subsystem 422 may include an infrared device and associated circuits and modules for short-range communication. Examples of short-range communication standards include standards developed by the Infrared Data Association (IrDA), Bluetooth, and the 802.11 family of standards developed by IEEE.

Bluetooth is a wireless technology standard for exchanging data over short distances (using short-wavelength radio transmissions in the ISM band from 2400-2480 MHz) from fixed and mobile devices, creating personal area networks (PANs) with high levels of security. Created by telecom vendor Ericsson in 1994, Bluetooth was originally conceived as a wireless alternative to RS-232 data cables. Bluetooth can connect several devices, overcoming problems of synchronization. Bluetooth operates in the range of 2400-2483.5 MHz (including guard bands), which is in the globally unlicensed Industrial, Scientific and Medical (ISM) 2.4 GHz short-range radio frequency band. Bluetooth uses a radio technology called frequency-hopping spread spectrum. The transmitted data is divided into packets and each packet is transmitted on one of the 79 designated Bluetooth channels. Each channel has a bandwidth of 1 MHz. The first channel starts at 2602 MHz and continues up to 2480 MHz in 1 MHz steps. The first channel usually performs 2200 hops per second, with Adaptive Frequency-Hopping (AFH) enabled. Originally Gaussian frequency-shift keying (GFSK) modulation was the only modulation scheme available; subsequently, since the introduction of Bluetooth 2.0+ EDR, $\pi/4$-DQPSK and 8DPSK modulation may also be used between compatible devices. Devices functioning with GFSK are said to be operating in basic rate (BR) mode where an instantaneous data rate of 1 Mbit/s is possible. The term Enhanced Data Rate (EDR) is used to describe $\pi/4$-DPSK and 8DPSK schemes, each giving 2 and 3 Mbit/s respectively. The combination of these (BR and EDR) modes in Bluetooth radio technology is classified as a "BR/EDR radio". Bluetooth is a packet-based protocol with a master-slave structure. One master may communicate with up to 7 slaves in a piconet; all devices share the master's clock. Packet exchange is based on the basic clock, defined by the master, which ticks at 312.5 µs intervals. Two clock ticks make up a slot of 625 µs; two slots make up a slot pair of 1250 µs. In the simple case of single-slot packets the master transmits in even slots and receives in odd slots; the slave, conversely, receives in even slots and transmits in odd slots. Packets may be 1, 3 or 5 slots long but in all cases the master transmit will begin in even slots and the slave transmit in odd slots. A master Bluetooth device can communicate with a maximum of seven devices in a piconet (an ad-hoc computer network using Bluetooth technology), though not all devices reach this maximum. The devices can switch roles, by agreement, and the slave can become the master (for example, a headset initiating a connection to a phone will necessarily begin as master, as initiator of the connection; but may subsequently prefer to be slave). The Bluetooth Core Specification provides for the connection of two or more piconets to form a scatternet, in which certain devices simultaneously play the master role in one piconet and the slave role in another. At any given time, data can be transferred between the master and one other device (except for the little-used broadcast mode. The master chooses which slave device to address; typically, the master switches rapidly from one device to another in a round-robin fashion.

Since the master chooses which slave to address, whereas a slave is (in theory) supposed to listen in each receive slot, being a master is a lighter burden than being a slave. Being a master of seven slaves is possible; being a slave of more than one master is difficult. Many of the services offered over Bluetooth can expose private data or allow the connecting party to control the Bluetooth device. For security reasons it is necessary to be able to recognize specific devices and thus enable control over which devices are allowed to connect to a given Bluetooth device. At the same time, it is useful for Bluetooth devices to be able to establish a connection without user intervention (for example, as soon as the Bluetooth devices of each other are in range). To resolve this conflict, Bluetooth uses a process called bonding, and a bond is created through a process called pairing. The pairing process is triggered either by a specific request from a user to create a bond (for example, the user explicitly requests to "Add a Bluetooth device"), or the pairing process is triggered automatically when connecting to a service where (for the first time) the identity of a device is required for security purposes. These two cases are referred to as dedicated bonding and general bonding respectively. Pairing often involves some level of user interaction; this user interaction is the basis for confirming the identity of the devices. Once pairing successfully completes, a bond will have been formed between the two devices, enabling those two devices to connect to each other in the future without requiring the pairing process in order to confirm the identity of the devices. When desired, the bonding relationship can later be removed by the user. Secure Simple Pairing (SSP): This is required by Bluetooth v2.1, although a Bluetooth v2.1 device may only use legacy pairing to interoperate with a v2.0 or earlier device. Secure Simple Pairing uses a form of public key cryptography, and some types can help protect against man in the middle, or MITM attacks. SSP has the following characteristics: Just works: As implied by the name, this method just works. No user interaction is required; however, a device may prompt the user to confirm the pairing process. This method is typically used by headsets with very limited IO capabilities, and is more secure than the fixed PIN mechanism which is typically used for legacy pairing by this set of limited devices. This method provides no man in the middle (MITM) protection. Numeric comparison: If both devices have a display and can accept a binary Yes/No user input, both devices may use Numeric Comparison. This method displays a 6-digit numeric code on each device. The user should compare the numbers to ensure that the numbers are identical. If the comparison succeeds, the user(s) should confirm pairing on the device(s) that can accept an input. This method provides MITM protection, assuming the user confirms on both devices and actually performs the comparison properly. Passkey Entry: This method may be used between a device with a display and a device with numeric keypad entry (such as a keyboard), or two devices with numeric keypad entry. In the first case, the display is used to show a 6-digit numeric code to the user, who then enters the code on the keypad. In the second case, the user of each device enters the same 6-digit number. Both of these cases provide MITM protection. Out of band (OOB): This method uses an external means of communication, such as Near Field Communication (NFC) to exchange some information used in the pairing process. Pairing is completed using the Bluetooth radio, but requires information from the OOB mechanism. This provides only the level of MITM protection that is present in the OOB mechanism. SSP is considered simple for the following reasons: In most cases, SSP does not require a user to generate a passkey. For use-cases not requiring MITM protection, user interaction can be eliminated. For numeric comparison, MITM protection can be achieved with a simple equality comparison by the user. Using OOB with NFC enables pairing when devices simply get close, rather than requiring a lengthy discovery process.

In use, a received signal such as a text message, an e-mail message, or web page download will be processed by the communication subsystem 404 and input to the main processor 402. The main processor 402 will then process the received signal for output to the display 410 or alternatively to the auxiliary I/O subsystem 412. A subscriber may also compose data items, such as e-mail messages, for example, using the keyboard 416 in conjunction with the display 410 and possibly the auxiliary I/O subsystem 412. The auxiliary I/O subsystem 412 may include devices such as: a touch screen, mouse, track ball, infrared fingerprint detector, or a roller wheel with dynamic button pressing capability. The keyboard 416 is preferably an alphanumeric keyboard and/or telephone-type keypad. However, other types of keyboards may also be used. A composed item may be transmitted over the wireless network 405 through the communication subsystem 404.

For voice communications, the overall operation of the hand-held device 400 is substantially similar, except that the received signals are output to the speaker 418, and signals for transmission are generated by the microphone 420. Alternative voice or audio I/O subsystems, such as a voice message recording subsystem, can also be implemented on the hand-held device 400. Although voice or audio signal output is accomplished primarily through the speaker 418, the display 410 can also be used to provide additional information such as the identity of a calling party, duration of a voice call, or other voice call related information.

Figure 5:
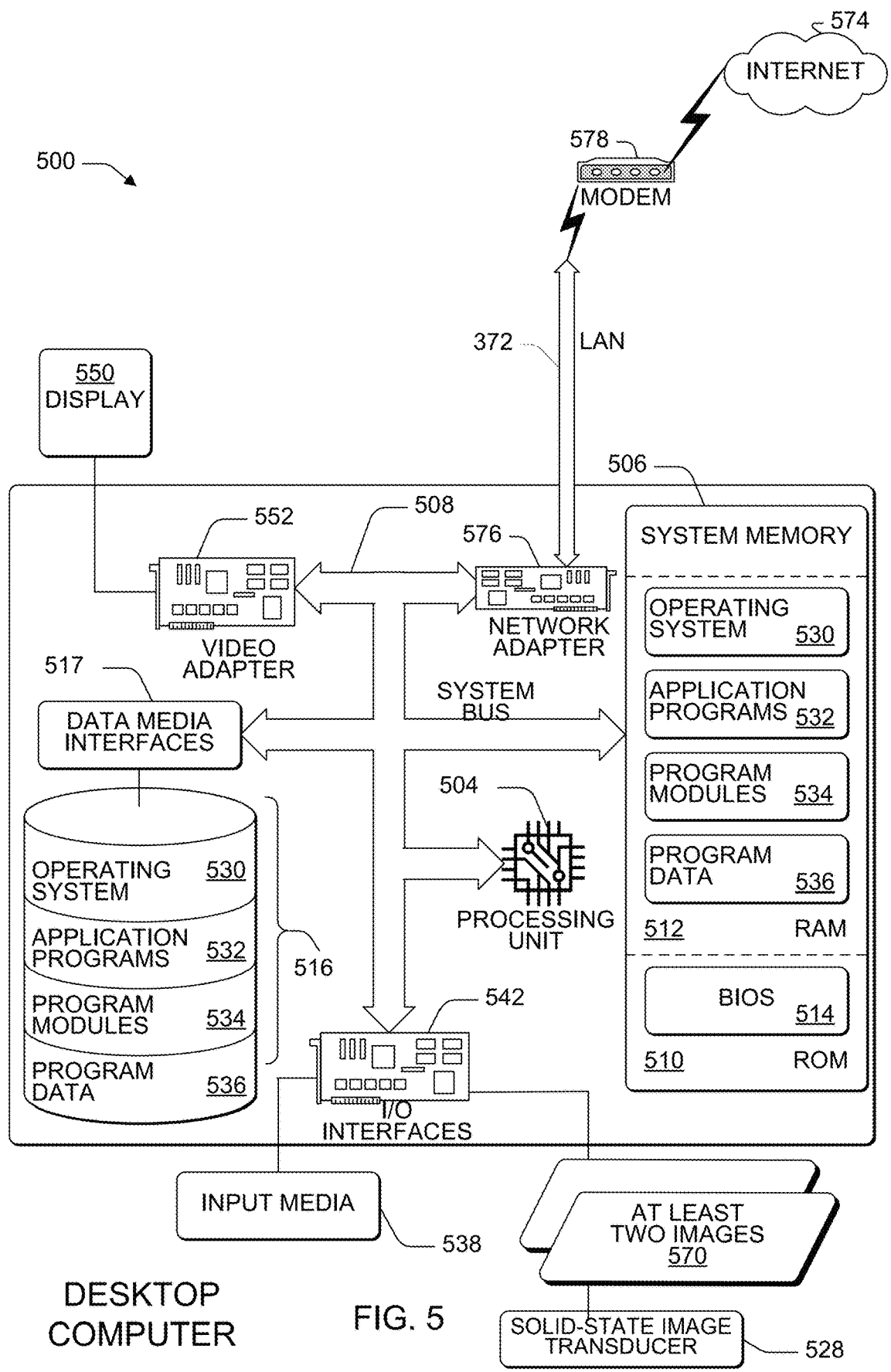
FIG. 5 is a block diagram of a hardware and operating computing system in which different implementations can be practiced, according to an implementation.

FIG. 5 is a block diagram of a hardware and operating computing system 500 in which different implementations can be practiced. The description of FIG. 5 provides an overview of computer hardware and a suitable computing environment in conjunction with which some implementations can be implemented. Implementations are described in terms of a computer executing computer-executable instructions. However, some implementations can be implemented entirely in computer hardware in which the computer-executable instructions are implemented in read-only memory. Some implementations can also be implemented in client/server computing environments where remote devices that perform tasks are linked through a communications network. Program modules can be located in both local and remote memory storage devices in a distributed computing environment.

FIG. 5 illustrates an example of a computing system 500 useful in the context of the environment of FIG. 1-2, in accordance with an implementation. It will be appreciated that other devices can alternatively be used that include more modules, or fewer modules, than those illustrated in FIG. 5.

The illustrated operating computing system 500 is only one example of a suitable operating environment, and the example described with reference to FIG. 5 is not intended to suggest any limitation as to the scope of use or functionality of the implementations of this disclosure. Other well-known computing systems, environments, and/or configurations can be suitable for implementation and/or application of the subject matter disclosed herein.

The computing system 500 includes one or more processors or processing units 504, a system memory 506, and a system bus 508 that couples various system modules including the system memory 506 to processing unit 504 and other elements in the computing system 500. The system bus 508 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols.

The system memory 506 includes nonvolatile read-only memory (ROM) 510 and random access memory (RAM) 512, which can or can not include volatile memory elements. A basic input/output system (BIOS) 514, containing the elementary routines that help to transfer information between elements within computing system 500 and with external items, typically invoked into operating memory during start-up, is stored in ROM 510.

The computing system 500 further can include a non-volatile read/write memory 516, represented in FIG. 5 as a hard disk drive, coupled to system bus 508 via a data media interface 517 (e.g., a SCSI, ATA, or other type of interface); a magnetic disk drive (not shown) for reading from, and/or writing to, a removable magnetic disk and an optical disk drive (not shown) for reading from, and/or writing to, a removable optical disk such as a CD, DVD, or other optical media.

The non-volatile read/write memory 516 and associated computer-readable media provide nonvolatile storage of computer-readable instructions, data structures, program modules and other data for the computing system 500. Although the computing system 500 is described herein as employing a non-volatile read/write memory 516, a removable magnetic disk and a removable optical disk, it will be appreciated by those skilled in the art that other types of computer-readable media which can store data that is accessible by a computer, such as magnetic cassettes, FLASH memory cards, random access memories (RAMs), read only memories (ROM), and the like, can also be used in the exemplary operating environment.

A number of program modules can be stored via the non-volatile read/write memory 516, removable magnetic disk, removable optical disk, ROM 510, or RAM 512, including an operating system 530, one or more application programs 532, program modules 534 and program data 536. Examples of computer operating systems conventionally employed include the NUCLEUS® operating system, the LINUX® operating system, and others, for example, providing capability for supporting application programs 532 using, for example, code modules written in the C++® computer programming language. The application programs 532 and/or the program modules 534 can also include a variance analytic module (as shown in 190 in FIGS. 1, 4 and 9). The multimedia document integration module 130 integrates documents from which the query module 150 generates inquiries and responses that are received from which the variance analytic module 190 generates the quantitative variance 195 that is displayed by display 550 or transmitted by computing system 500, enunciated by a speaker or stored in program data 536. Some implementations of the computing system 500 include a solid-state image transducer 528 that is operably coupled to the processing unit 504 and is operable to provide two or more images 570 to the multimedia document integration module 130 in the application programs 532 and/or the program modules 534.

A user can enter commands and information into computing system 500 through input devices such as input media 538 (e.g., keyboard/keypad, tactile input or pointing device, mouse, foot-operated switching apparatus, joystick, touchscreen or touchpad, microphone, antenna etc.). Such input media 538 are coupled to the processing unit 504 through a conventional input/output interface 542 that is, in turn, coupled to the system bus 508. Display 550 or other type of display device is also coupled to the system bus 508 via an interface, such as a video adapter 552.

The computing system 500 can include capability for operating in a networked environment using logical connections to one or more remote computers, such as a remote computer. The remote computer can be a personal computer, a server, a router, a network PC, a peer device or other common network node, and typically includes many or all of the elements described above relative to the computing system 500. In a networked environment, program modules depicted relative to the computing system 500, or portions thereof, can be stored in a remote memory storage device such as can be associated with the remote computer. By way of example, remote application programs reside on a memory device of the remote computer. The logical connections represented in FIG. 5 can include interface capabilities, a storage area network (SAN, not illustrated in FIG. 5), local area network (LAN) 372 and/or a wide area network (WAN), but can also include other networks.

Such networking environments are commonplace in modern computer systems, and in association with intranets and the Internet. In certain implementations, the computing system 500 executes an Internet Web browser program (which can optionally be integrated into the operating system 530), such as the "Internet Explorer®" Web browser manufactured and distributed by the Microsoft Corporation of Redmond, Wash.

When used in a LAN-coupled environment, the computing system 500 communicates with or through the local area network 372 via a network interface or adapter 576 and typically includes interfaces, such as a modem 578, or other apparatus, for establishing communications with or through the WAN 574, such as the Internet. The modem 578, which can be internal or external, is coupled to the system bus 508 via a serial port interface.

In a networked environment, program modules depicted relative to the computing system 500, or portions thereof, can be stored in remote memory apparatus. It will be appreciated that the network connections shown are exemplary, and other means of establishing a communications link between various computer systems and elements can be used.

A user of a computer can operate in a networked environment using logical connections to one or more remote computers, such as a remote computer, which can be a personal computer, a server, a router, a network PC, a peer device or other common network node. Typically, a remote computer includes many or all of the elements described above relative to the computing system 500 of FIG. 5.

The computing system 500 typically includes at least some form of computer-readable media. Computer-readable media can be any available media that can be accessed by the computing system 500. By way of example, and not limitation, computer-readable media can comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computing system 500.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media include wired media, such as wired network or direct-wired connections, and wireless media, such as acoustic, RF, infrared and other wireless media. The scope of the term computer-readable media includes combinations of any of the above.

Figure 6:
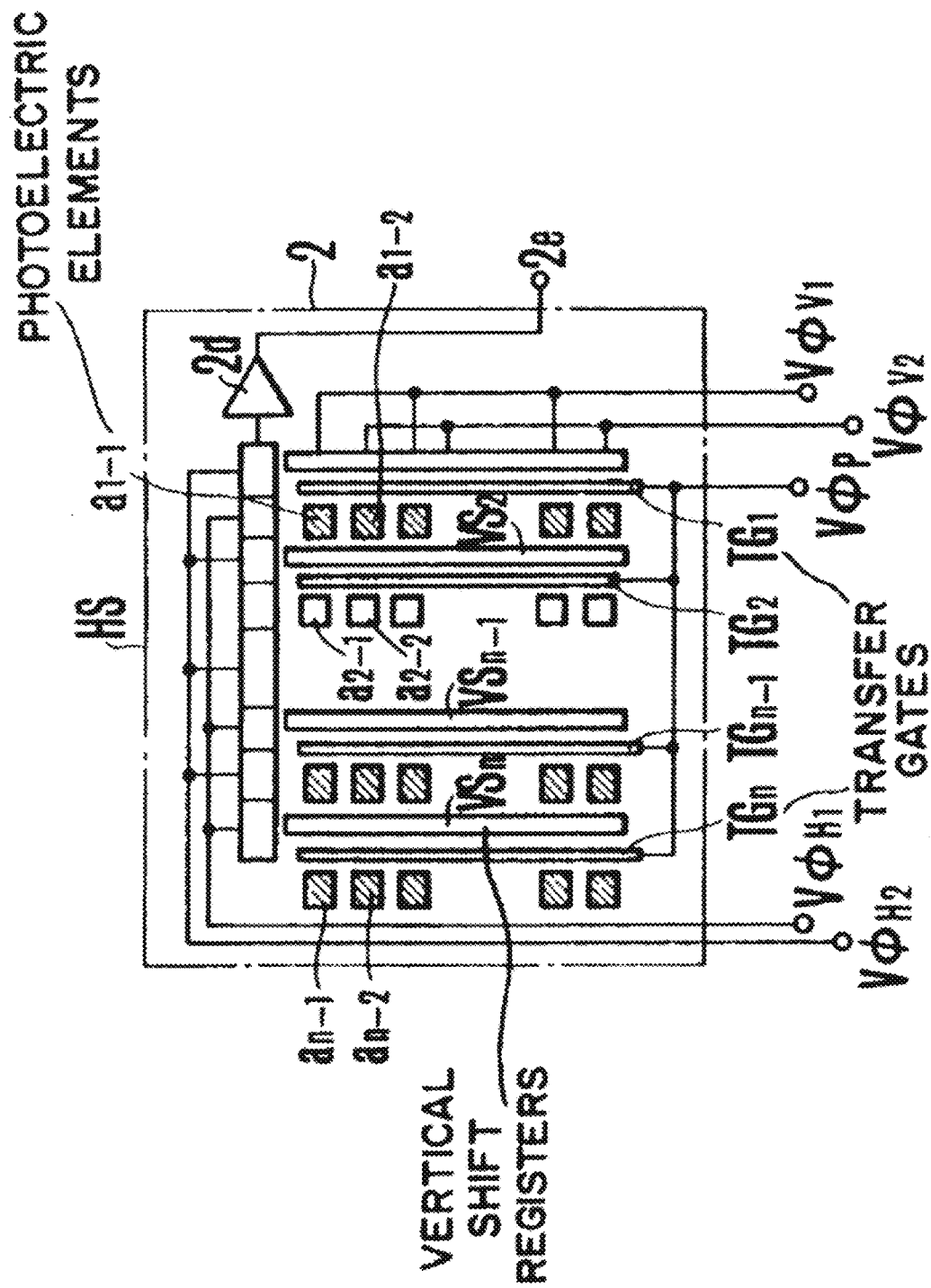
FIG. 6 is a block diagram of a solid-state image transducer, according to an implementation.

FIG. 6 is a block diagram of a solid-state image transducer 600, according to an implementation. The solid-state image transducer 600 includes a great number of photoelectric elements, $a.sub.1..sub.1, a.sub.2..sub.1, \ldots, a.sub.mn$, in the minute segment form, transfer gates TG1, TG2, . . . , TGn responsive to a control pulse $V.sub.\varphi P$ for transferring the charges stored on the individual photoelectric elements as an image signal to vertical shift registers VS1, VS2, . . . , VSn, and a horizontal shift register HS for transferring the image signal from the vertical shift registers VSs, through a buffer amplifier 2d to an outlet 2e. After the one-frame image signal is stored, the image signal is transferred to vertical shift register by the pulse $V.sub.\varphi P$ and the contents of the vertical shift registers VSs are transferred upward line by line in response to a series of control pulses $V.sub.\varphi V1$, $V.sub.\varphi V2$. During the time interval between the successive two vertical transfer control pulses, the horizontal shift register HS responsive to a series of control pulses $V.sub.\varphi H1, V.sub.\varphi H2$ transfers the contents of the horizontal shift registers HSs in each line row by row to the right as viewed in FIG. 6. As a result, the one-frame image signal is formed by reading out the outputs of the individual photoelectric elements in such order.

Figure 7:
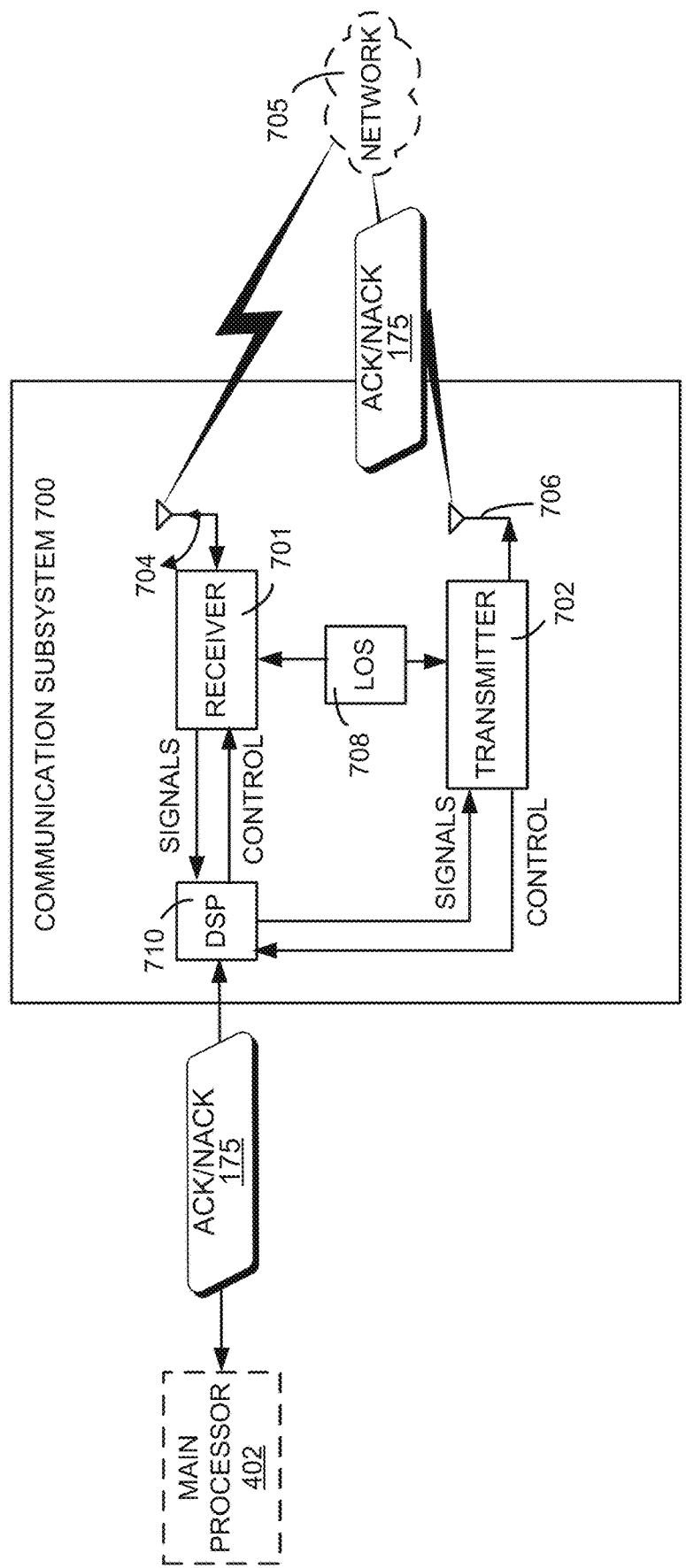
FIG. 7 is a block diagram of the wireless communication subsystem, according to an implementation.

FIG. 7 is a block diagram of the wireless communication subsystem 700, according to an implementation. The communication subsystem 700 is one example of the communication subsystem 170 in FIG. 1 and the communication subsystem 404 in FIG. 4. The wireless communication subsystem 700 includes a receiver 701, a transmitter 702, as well as associated components such as one or more embedded or antennas 704 and 706, Local Oscillators (LOs) 708, and a processing module such as a digital signal processor (DSP) 710. The particular implementation of the wireless communication subsystem 700 is dependent upon communication protocols of a wireless network 705 with which the mobile device is intended to operate. Thus, it should be understood that the implementation illustrated in FIG. 7 serves only as one example. Examples of the client device 204 include hand-held device 400, computer 500 and tablet 800. Examples of the wireless network 705 include network 405 in FIG. 4.

Signals received by the antenna 704 through the wireless network 705 are input to the receiver 701, which may perform such common receiver functions as signal amplification, frequency down conversion, filtering, channel selection, and analog-to-digital (A/D) conversion. A/D conversion of a received signal allows more complex communication functions such as demodulation and decoding to be performed in the DSP 710. In a similar manner, signals to be transmitted are processed, including modulation and encoding, by the DSP 710. These DSP-processed signals are input to the transmitter 702 for digital-to-analog (D/A) conversion, frequency up conversion, filtering, amplification and transmission over the wireless network 705 via the antenna 706. The DSP 710 not only processes communication signals, but also provides for receiver and transmitter control. For example, the gains applied to communication signals in the receiver 701 and the transmitter 702 may be adaptively controlled through automatic gain control algorithms implemented in the DSP 710.

The wireless link between the client device 204 and the wireless network 705 can contain one or more different channels, typically different RF channels, and associated protocols used between the client device 204 and the wireless network 705. An RF channel is a limited resource that must be conserved, typically due to limits in overall bandwidth and limited battery power of the client devices 204.

When the client device 204 is fully operational, the transmitter 702 is typically keyed or turned on only when it is transmitting to the wireless network 705 and is otherwise turned off to conserve resources. Similarly, the receiver 701 is periodically turned off to conserve power until the receiver 701 is needed to receive signals or information (if at all) during designated time periods.

The ACK/NACK transmission 175 is received by the wireless communication subsystem 700 from the main processor (304, 402 or 504) at the DSP 710 and then transmitted to the wireless network 705 through the antenna 704 of the receiver 701.

Figure 8:
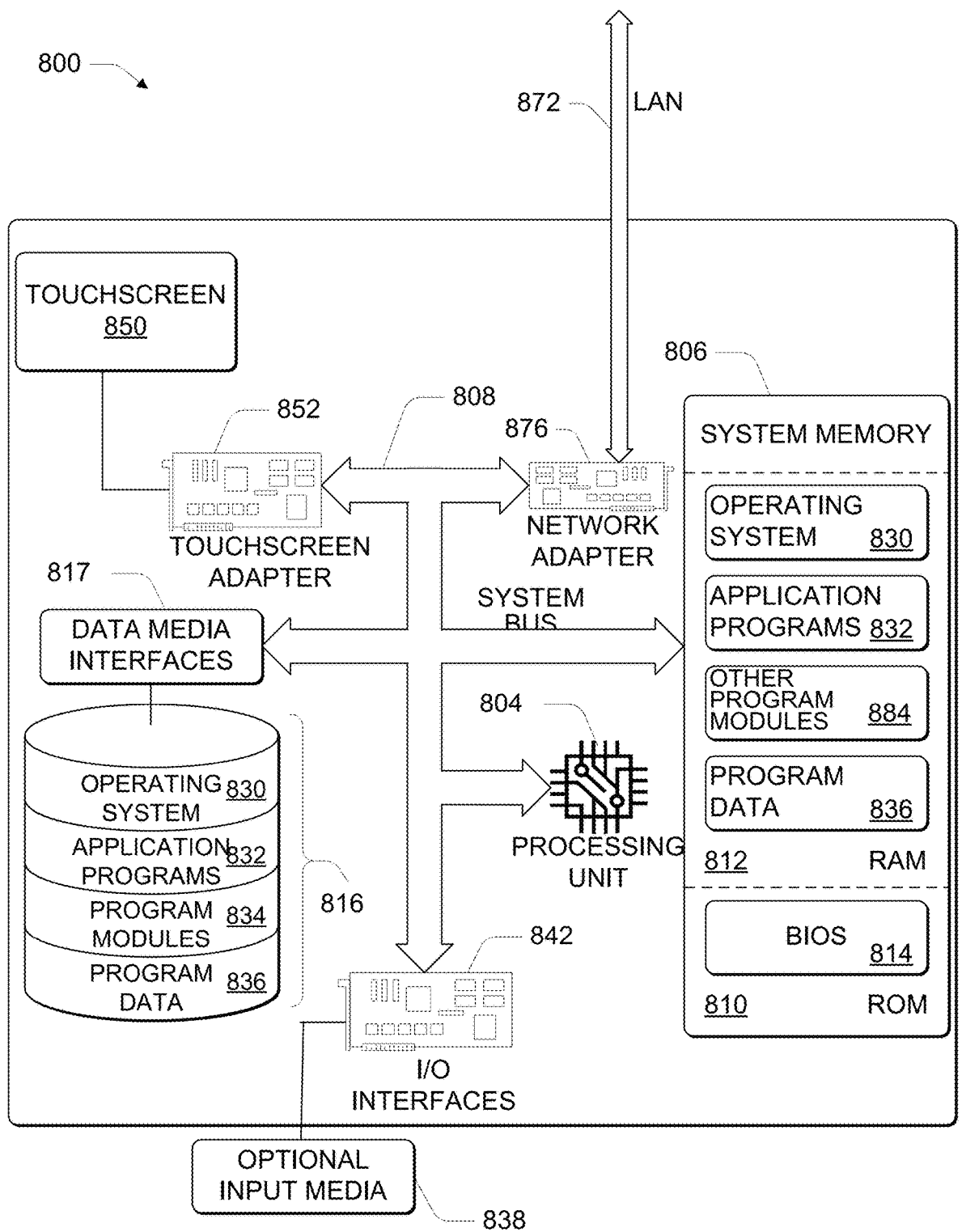
FIG. 8 is a block diagram of a tablet computer, according to an implementation.

FIG. 8 is a block diagram of a tablet computer 800, according to an implementation. The description of FIG. 8 provides an overview of computer hardware and a suitable computing environment in conjunction with which some implementations can be implemented. Implementations are described in terms of a computer executing computer-executable instructions. However, some implementations can be implemented entirely in computer hardware in which the computer-executable instructions are implemented in read-only memory. Some implementations can also be implemented in client/server computing environments where remote devices that perform tasks are linked through a communications network. Program modules can be located in both local and remote memory storage devices in a distributed computing environment.

Figure 10:
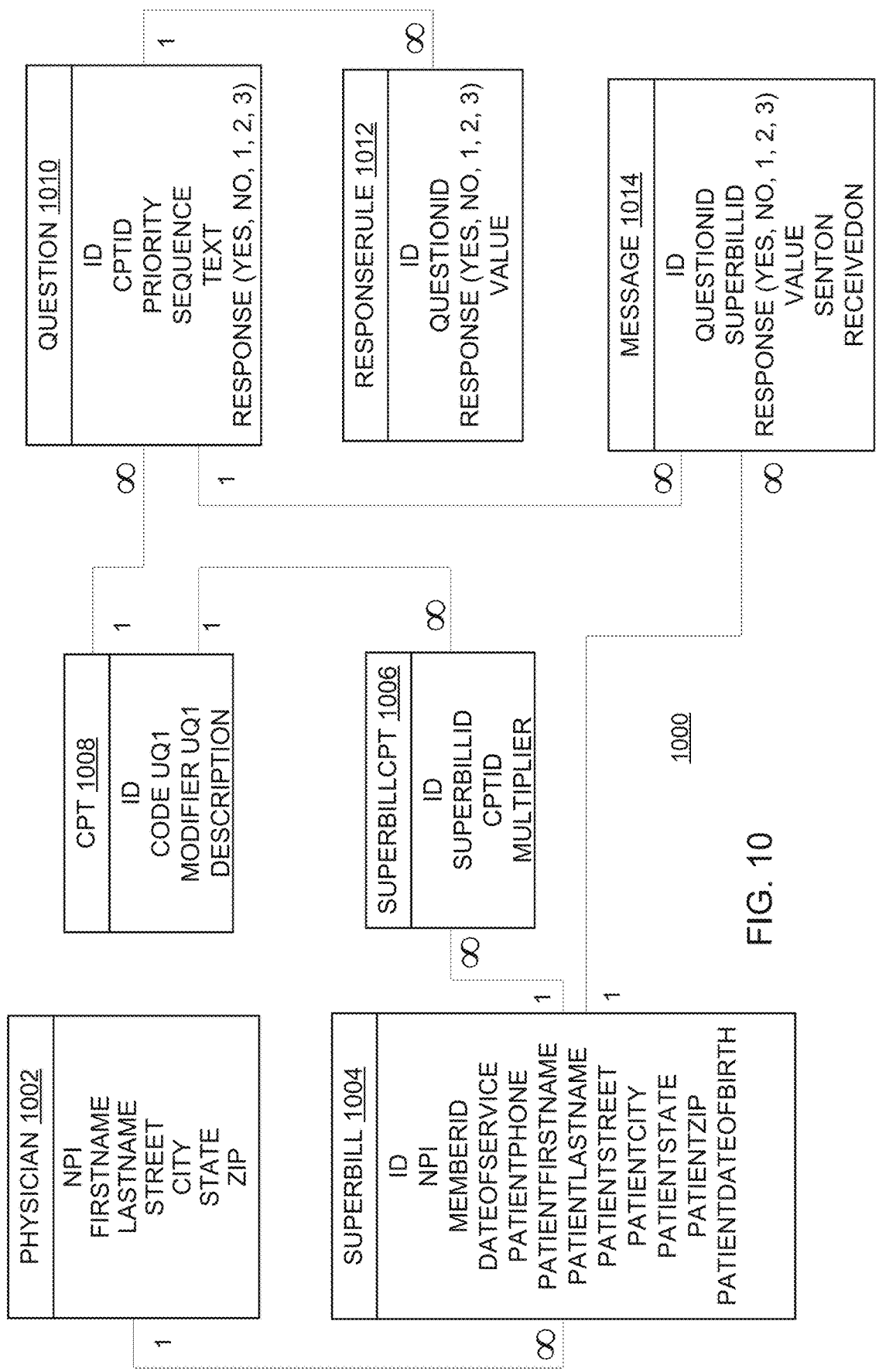
FIG. 10 is a block diagram of a database entity relationship system, according to an implementation.

FIG. 8 illustrates an example of a tablet computer 800 useful in the context of the processes and components in FIGS. 1 and 9-10, in accordance with an implementation. It will be appreciated that other devices can alternatively be used that include more components, or fewer components, than those illustrated in FIG. 8.

The illustrated tablet computer 800 is only one example of a suitable operating environment, and the example described with reference to FIG. 8 is not intended to suggest any limitation as to the scope of use or functionality of the implementations of this disclosure. Other well-known computing systems, environments, and/or configurations can be suitable for implementation and/or application of the subject matter disclosed herein.

The tablet computer 800 includes one or more processors or processing units 804, a system memory 806, and a bus 808 that couples various system components including the system memory 806 to processors or processing units 804 and other elements in the tablet computer 800. The bus 808 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols.

The system memory 806 includes nonvolatile read-only memory (ROM) 810 and random access memory (RAM) 812, which can or can not include volatile memory elements. A basic input/output system (BIOS) 814, containing the elementary routines that help to transfer information between elements within tablet computer 800 and with external items, typically invoked into operating memory during start-up, is stored in ROM 810.

The tablet computer 800 further can include a FLASH memory 816 that is coupled to bus 808 via a data media interface 817 (e.g., a SCSI, ATA, or other type of interface); a magnetic disk drive (not shown) for reading from, and/or writing to, a removable magnetic disk (not shown) and an optical disk drive (not shown) for reading from, and/or writing to, a removable optical disk (not shown) such as a CD, DVD, or other optical media.

The FLASH memory 816 and associated computer-readable media provide nonvolatile storage of computer-readable instructions, data structures, program modules and other data for the tablet computer 800.

A number of program modules can be stored via the FLASH memory 816, magnetic disk (not shown), optical disk (not shown), ROM 810, or RAM 812, including an operating system 830, one or more application programs 832, other program modules 834 and program data 836. Examples of computer operating systems conventionally employed include the NUCLEUS® operating system, the LINUX® operating system, and others, for example, providing capability for supporting application programs 832 using, for example, code modules written in the C++® computer programming language.

A user can optionally enter commands and information into tablet computer 800 through input devices such as external input media 838 (e.g., keyboard/keypad, tactile input or pointing device, mouse, foot-operated switching apparatus, joystick, touchscreen or touchpad, microphone, antenna etc.). Such input devices 838 are coupled to the processors or processing units 804 through a conventional input/output interface 842 that is, in turn, coupled to the system bus. A touchscreen 850 or other type of display device is also coupled to the system bus 808 via an interface, such as a touchscreen adapter 852.

The tablet computer 800 can include capability for operating in a networked environment using logical connections to one or more remote computers. The remote computer can be a personal computer, a server, a router, a network PC, a peer device or other common network node, and typically includes many or all of the elements described above relative to the tablet computer 800. In a networked environment, program modules depicted relative to the tablet computer 800, or portions thereof, can be stored in a remote memory storage device such as can be associated with the remote computer. By way of example, remote application programs reside on a memory device of the remote computer. The logical connections represented in FIG. 8 can include interface capabilities, e.g., such as interface capabilities in FIG. 8, a storage area network (SAN, not illustrated in FIG. 8), local area network (LAN) 872 and/or a wide area network (WAN), but can also include other networks.

Such networking environments are commonplace in modern computer systems, and in association with intranets and the Internet. In certain implementations, the tablet computer 800 executes an Internet Web browser program (which can optionally be integrated into the operating system 830), such as the "Internet Explorer®" Web browser manufactured and distributed by the Microsoft Corporation of Redmond, Wash. When used in a LAN-coupled environment, the tablet computer 800 communicates with or through the local area network 872 via a network interface or adapter 876. When used in a WAN-coupled environment, the tablet computer 800 typically includes interfaces, or other apparatus, for establishing communications with or through the WAN, such as the Internet. The modem, which can be internal or external, is coupled to the system bus 808 via a serial port interface. In a networked environment, program modules depicted relative to the tablet computer 800, or portions thereof, can be stored in remote memory apparatus. It will be appreciated that the network connections shown are exemplary, and other means of establishing a communications link between various computer systems and elements can be used. A user of a computer can operate in a networked environment using logical connections to one or more remote computers, such as a remote computer, which can be a personal computer, a server, a router, a network PC, a peer device or other common network node. Typically, a remote computer includes many or all of the elements described above relative to the tablet computer 800 of FIG. 8. The tablet computer 800 typically includes at least some form of computer-readable media. Computer-readable media can be any available media that can be accessed by the tablet computer 800. By way of example, and not limitation, computer-readable media can comprise computer storage media and communication media. Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the tablet computer 800.

FIG. 9 is a block diagram of a multimedia document interchange variance detection system 900 to exchange information in a predetermined architecture of multimedia object interchange, according to an implementation.

The multimedia document interchange variance detection system 900 receives a multimedia document 110 and optionally another multimedia document 120 into a carrier integration module 930. In some implementations, the multimedia document 110 and the multimedia document 120 are insurance medical claims that include CPT codes and that do not include audio or video data. The carrier integration module 930 integrates the multimedia document 110 and the multimedia document 120, generating an integrated multimedia document 135. The integrated multimedia document 135 is received by a data capture module 140 and extracts field of capture data 945 from the integrated multimedia device-independent document 135. An external patient question module 950 receives the extracted field of capture data 945 from the data capture module 140 and generates one or more queries that are encapsulated in a corresponding number of inquiry transmission(s) 960. The multimedia document interchange variance detection system 900 also includes a semantic translation module 965 that is operable to translate the inquiry transmission(s) 960 from one language to another, such as from English language to the indicated language of the patient, such as Spanish. The inquiry transmission(s) 960 are received by a patient engagement system 970, the patient engagement system 970 transmits the inquiry transmission(s) 960 to an external device (such as client device 204 as described in greater detail in FIG. 2) and the external device (e.g. client devices 204) responds with a response transmission 975. In some implementations, the response is a single character message indicating acknowledgement of the corresponding Inquiry transmission 960. In some implementations, a negative response is not implemented, but instead the absence of a response from the external device is interpreted by the patient engagement system 970 as a negative response. The response 975 is stored in a patient response database 980. A variance analytic module 190 retrieves the response 975 from the patient response database 980 and the variance analytic module 190 generates a quantitative variance 195 from the retrieved Response 975. The quantitative variance 195 describes variances and discrepancies within the multimedia document 110 and within the multimedia document 120 and between the multimedia document 110 and the multimedia document 120.

FIG. 10 is a block diagram of a database entity relationship system 1000, according to an implementation. The database entity relationship system 1000 is one example of the interaction database 208 and the interaction database 210. The database entity relationship system 1000 includes physician "(healthcare provider) table 1002 that has a one-to-many relationship to a superbill table 1004. Each entry or record in the physician table physician (or healthcare provider) table 1002 includes fields describing a Npi, a first name, a last name, a street, a city, a state and a zip code. Some implementations of the physician table 1002 is more generally a provider table. Each entry or record in the superbill table 1004 includes an identification, a Npi, a member identification, a date of service, a patient phone, a patient first name, a patient last name, a patient street, a patient city, a patient state, a patient zip and a patient zip code. Some implementations of the superbill table 1004 also include a patient social security number, a status (open, closed or expired) and a total amount of charges in the superbill table 1004. The superbill table 1004 has a one-to-many relationship to a superbill CPT table 1006. Each entry or record in the superbill CPT table 1006 has an identification, a superbill identification, a CPT identification and multiplier. Some implementations of the superbill CPT table 1006 also include a total amount of charges in the superbill CPT table 1006. A CPT table 1008 has a one-to-many relationship to the superbill CPT table 1006. Each entry or record in the CPT table 1008 has an identification, a code uq1, a modifier uq1 and a description. The CPT table 1008 has a one-to-many relationship to a question table 1010. Each entry or record in the question table 1010 has an identifier, a CPT identification, a sequence, a text field, a priority, and a previous response, (the previous response being a wide variety of expressions that are normalized to yes, no, or a numerical range such as 1, 2 or 3 [such as 'yeah' that is normalized to yes or 'nope' that is normalized to 'no' or 'n' that is normalized to 'no']). The question table 1010 has a one-to-many relationship to a Response Rule table 1012. Each entry or record in the Response Rule table 1012 includes an identifier, a question identification, a response and a value, (the response being limited to yes, no, 1, 2 or 3 a wide variety of expressions that are normalized to yes, no, or a numerical range such as 1, 2 or 3 [such as 'yeah' that is normalized to yes or 'nope' that is normalized to 'no' or 'n' that is normalized to 'no']). Some implementations of the Response Rule table 1012 also include a Response CPT Code. The question table 1010 and the superbill table 1004 have a one-to-many relationship to a message table 1014. Each entry or record in the message table 1014 includes an identifier, a question identification, a superbill identification, a response, a value, a date sent on and date received on, (the response being a wide variety of expressions that are normalized to yes, no, or a numerical range such as 1, 2 or 3 [such as 'yeah' that is normalized to yes or 'nope' that is normalized to 'no' or 'n' that is normalized to 'no']). Some implementations of the message table 1014 also include a Response CPT Code, a SentTwillioSid code, a ReceivedTwillioSid code and a status code (open, sent, received or closed).

Figure 11:
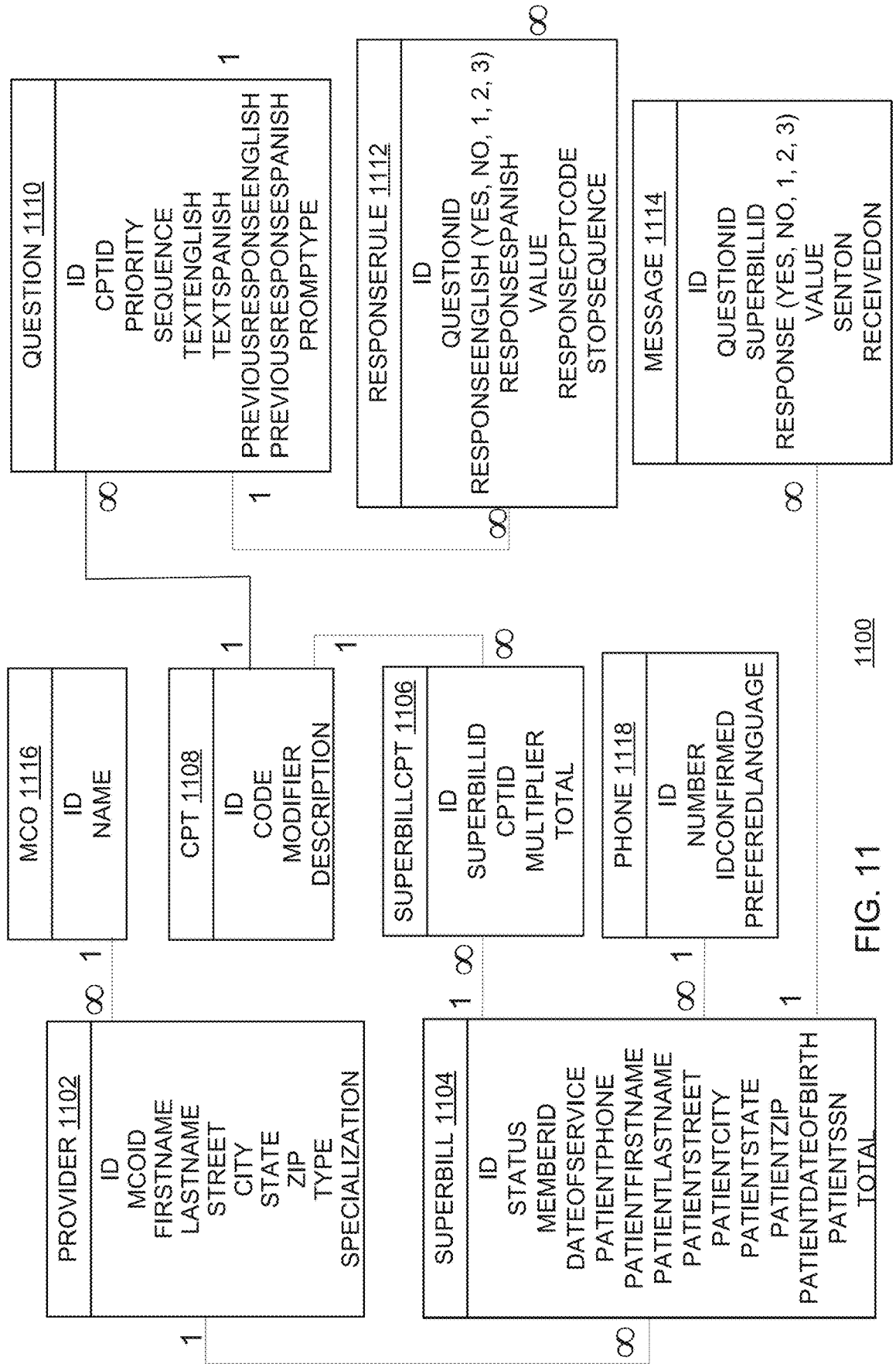
FIG. 11 is a block diagram of a database entity relationship system, according to an implementation.

FIG. 11 is a block diagram of a database entity relationship system 1100, according to an implementation. The database entity relationship system 1100 is one example of the interaction database 208 and the interaction database 210. The database entity relationship system 1100 includes provider table 1102 that has a one-to-many relationship to a superbill table 1104. Each entry or record in the provider table 1102 includes fields describing an ID, a MCO ID, a first name, a last name, a street, a city, a state, zip code type and a specialization. Some implementations of the provider table 1102 is more generally a provider table. Each entry or record in the superbill table 1104 includes an identification, a Npi, a status, a member identification, a date of service, a patient phone, a patient first name, a patient last name, a patient street, a patient city, a patient state, a patient zip, patient zip code. Some implementations of the superbill table 1104 also include a patient social security number, a status (open, closed or expired) and a total amount of charges in the superbill table 1104. The superbill table 1104 has a one-to-many relationship to a superbill CPT table 1106. Each entry or record in the superbill CPT table 1106 has an identification, a superbill identification, a CPT identification, a multiplier and a total. Some implementations of the superbill CPT table 1106 also include a total amount of charges in the superbill CPT table 1106. A CPT table 1108 has a one-to-many relationship to the superbill CPT table 1106. Each entry or record in the CPT table 1108 has an identification, a code, a modifier and a description. The CPT table 1108 has a one-to-many relationship to a question table 1110. Each entry or record in the question table 1110 has an identifier, a CPT identification, a sequence, a text-English field, a text-Spanish, a previous response English, (the previous response being a wide variety of expressions that are normalized to yes, no, or a numerical range such as 1, 2 or 3 [such as 'yeah' that is normalized to yes or 'nope' that is normalized to 'no' or 'n' that is normalized to 'no']), previous response Spanish and a prompt type. The question table 1010 has a one-to-many relationship to a Response Rule table 1012. Each entry or record in the Response Rule table 1112 includes an identifier, a question identification, a response English, (the response being a wide variety of expressions that are normalized to yes, no, or a numerical range such as 1, 2 or 3 [such as 'yeah' that is normalized to yes or 'nope' that is normalized to 'no' or 'n' that is normalized to 'no']), a response Spanish, a value, a response CPT code and a stop sequence. Some implementations of the Response Rule table 1112 also include a Response CPT Code. The question table 1110 and the superbill table 1104 have a one-to-many relationship to a message table 1114. Each entry or record in the message table 1114 includes an identifier, a question identification, a superbill identification, a response, a value, a date sent on, a date received on, (the response being a wide variety of expressions that are normalized to yes, no, or a numerical range such as 1, 2 or 3 [such as 'yeah' that is normalized to yes or 'nope' that is normalized to 'no' or 'n' that is normalized to 'no']). Some implementations of the message table 1114 also include a Response CPT Code, a SentTwillioSid code, a ReceivedTwillioSid code and a status code (open, sent, received or closed). The superbill table 1104 has a many-to-one relationship to a Phone table 1118. Each entry or record in the Phone table 1118 includes an identifier, a number, an identity confirmed and a preferred language.

Method Implementations

In the previous section, a system level overview of the operation of an implementation is described. In this section, the particular methods of such an implementation are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. Methods are performed by a program executing on, or performed by firmware or hardware that is a part of, a computer, such as variance detection server 300 in FIG. 3.

In other implementations, methods are implemented as a computer-accessible medium having executable instructions capable of directing a processor, such as processing unit 304 in FIG. 3, to perform the respective method. In varying implementations, the medium is a magnetic medium, an electronic medium, or an optical medium.

Figure 12:
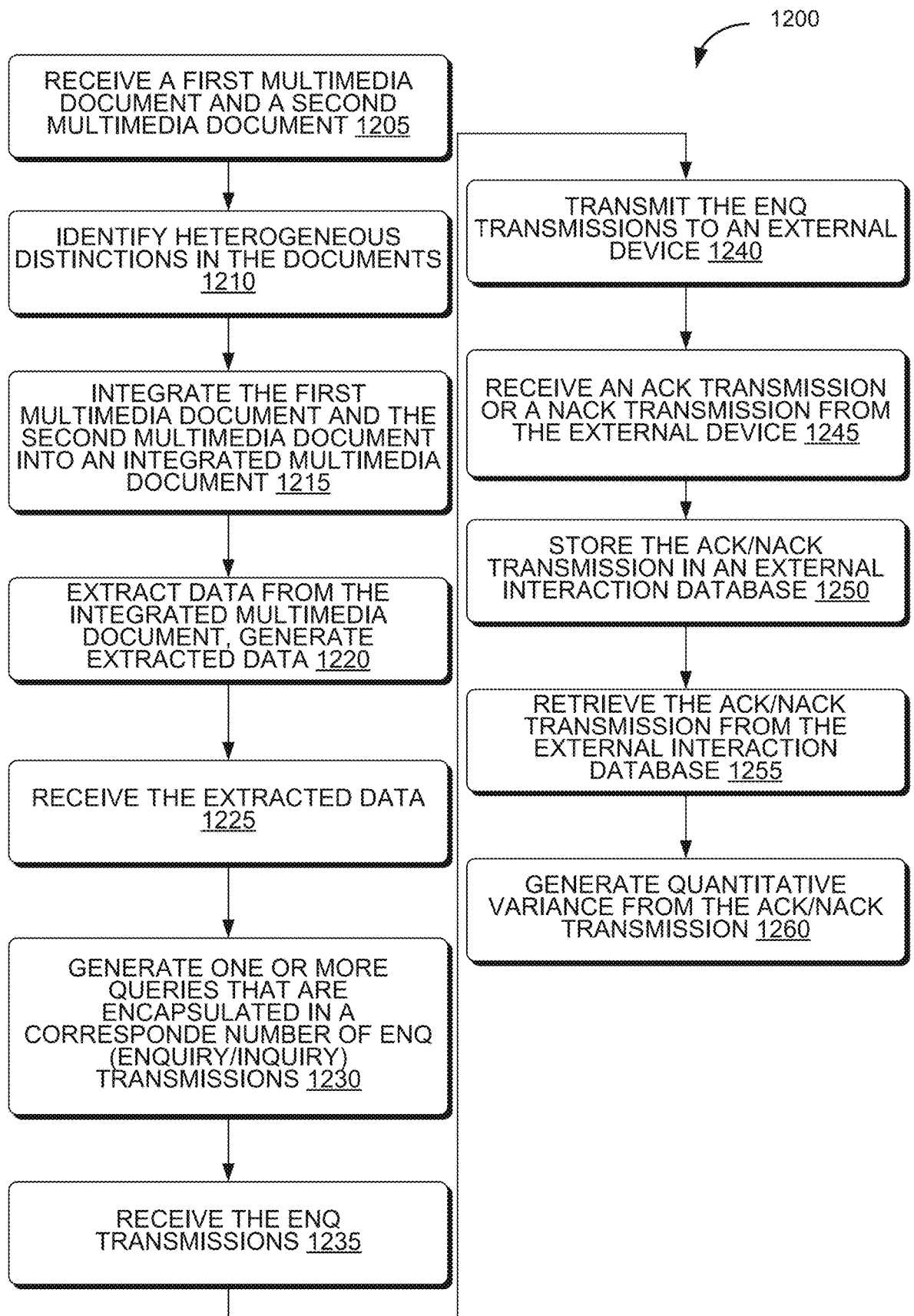
FIG. 12 is a block diagram of a method of multimedia document interchange variance detection, according to an implementation.

FIG. 12 is a block diagram of a method of multimedia document interchange variance detection 1200, according to an implementation.

Method 1200 includes receiving a first multimedia document and a second multimedia document, at block 1205. The first multimedia document and the second multimedia document received from heterogeneous computer systems. The first multimedia document and the second multimedia document having heterogeneous file formats, the first multimedia document having a heterogeneous internal organization to the second multimedia document.

Method 1200 also includes identifying heterogeneous distinctions, at block 1210. Method 1200 also includes integrating the first multimedia document and the second multimedia document into an integrated multimedia document, generating an integrated multimedia document, at block 1215. Method 1200 also includes extracting data from the integrated multimedia document, generating extracted data, at block 1220. Method 1200 also includes receiving the extracted data, at block 1225. Method 1200 also includes generating one or more queries that are encapsulated in a corresponding number of ENQ (enquiry/inquiry) transmissions, at block 1230, the ENQ transmissions being short-message-service (SMS) text messages. Method 1200 also includes receiving the ENQ transmissions, at block 1235. Method 1200 also includes transmitting the ENQ transmissions to an external device, at block 1240. Method 1200 also includes receiving an ACK (acknowledgement) transmission or a NACK (negative [not] acknowledgement) transmission from the external device, the ACK/NACK transmission being a SMS text message, at block 1245. Method 1200 also includes storing the ACK/NACK transmission in an external interaction database, at block 1250. Method 1200 also includes retrieving the ACK/NACK transmission from the external interaction database, at block 1255. Method 1200 also includes and generating quantitative variance from the ACK/NACK transmission, at block 1260. The quantitative variance describing statistical variances and discrepancies within the first multimedia document and within the second multimedia document and between the first multimedia document and the second multimedia document.

Figure 13:
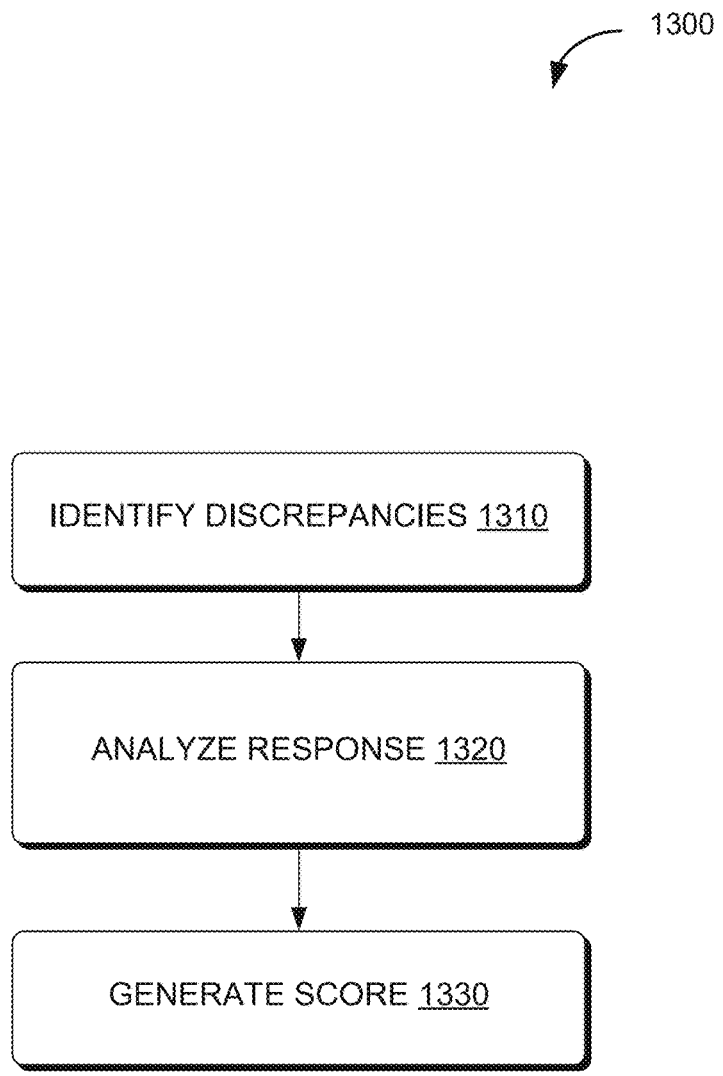
FIG. 13 is a block diagram of a method of discrepancy detection, according to an implementation.

FIG. 13 is a block diagram of a method of discrepancy detection 1300, according to an implementation. At block 1310 of method 1300, a billing code (e.g. CPT code), a priority code (overall high level priority that takes precedence over everything else), a sequence code (indicating if a question is a follow-up question), and a previous response (indicating whether or not the question requires a previous response) are evaluated for discrepancies. Every billing item in a document 120 or 130 includes a billing code and performance time of the procedure. In some implementations, discrepancies are identified between the billing code in the integrated multimedia document 135 and the ACK/NACK transmission 175. In other implementations, discrepancies are identified between the billing code in the integrated multimedia document 135 and the ACK/NACK transmission 175 that are at or above a predetermined threshold of the provider identified in the integrated multimedia document 135.

Thereafter, a response is evaluated and analyzed, at block 1320, such as evaluating and analyzing the significance of the lack of response (the lack of a ACK/NACK transmission 175) to a ENQ transmission(s) 160 that corresponds to a billing code in the integrated multimedia document 135 and the ACK/NACK transmission 175. In another implementation, lack of response (the lack of a ACK/NACK transmission 175) to a ENQ transmission(s) 160 that corresponds to a billing code in the integrated multimedia document 135 are at or above a predetermined threshold of a particular provider, is evaluated and analyzed.

Subsequently, a score is generated for a particular provider in reference to the identified responses and the identified discrepancies, at block 1330, resulting in a provider discrepancy score.

Methods 1400, 1500, 1600 and 1700 can be performed by the query module 150, the communication subsystem 170 and the patient engagement system 970 between the network 211 and the client device 204.

Figure 14:
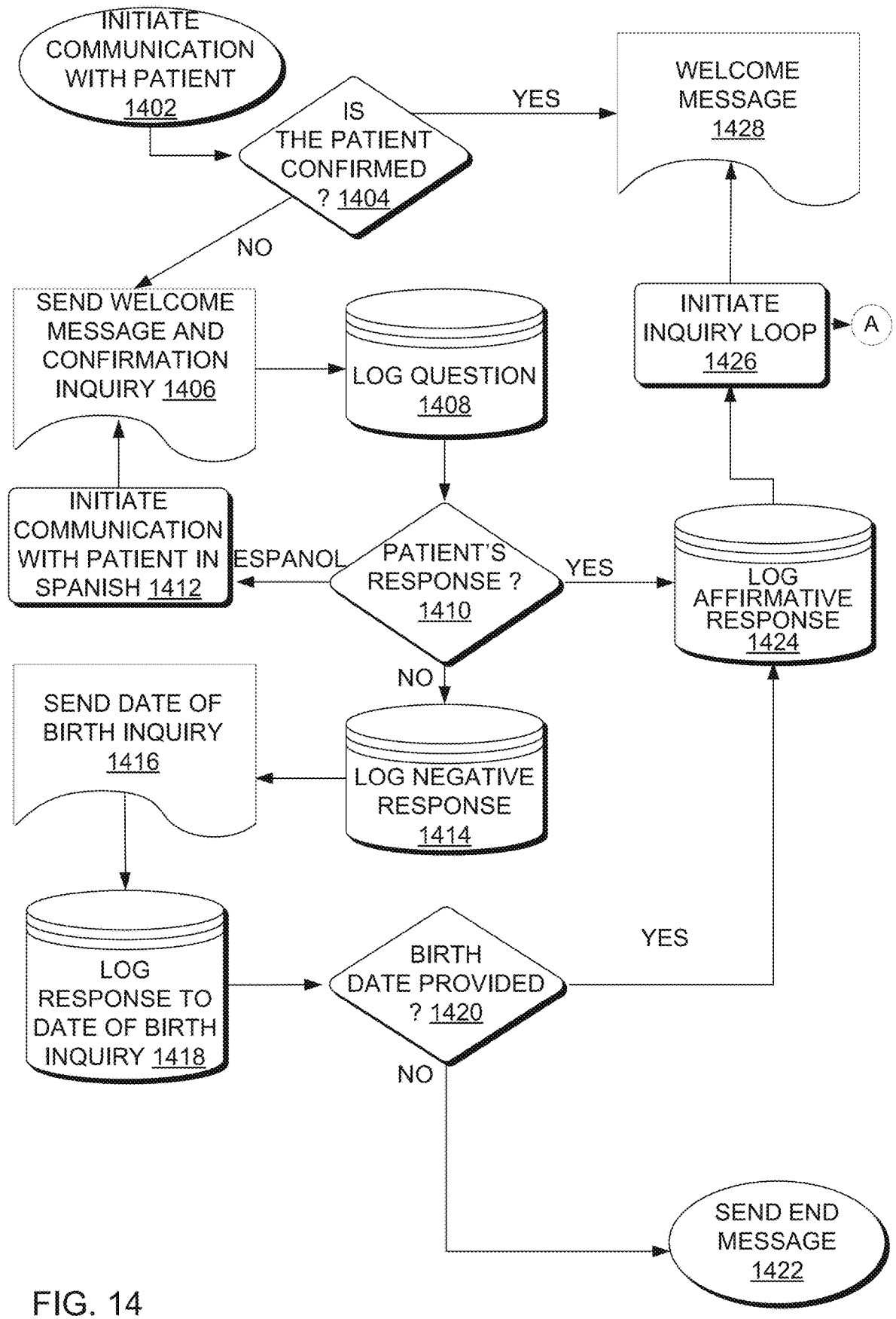
FIG. 14 is a block diagram of a method of inquiry, according to an implementation.

FIG. 14 is a block diagram of a method of inquiry 1400, according to an implementation. Method 1400 includes initiating communication with a patient at block 1402 and then determining if the patient is confirmed at block 1404. If the patient is not confirmed, then the method includes sending a welcome message and a confirmation inquiry at block 1406 and then logging a question at block 1408 and evaluating at block 1410 a response from the patient to determine if the response is in Spanish. If the response is in Spanish, then communication is initiated in Spanish at block 1412 and the methods 1400 and 1500 continues in the Spanish language. If the patient's response to the question is negative, then the negative response is logged at block 1414 and an inquiry as to the birthdate is sent at block 1416 and the response to the inquiry on the birthdate is logged at block 1418 then a determination is made as to whether or not the birth date was provided at block 1420. If no birthday was provided a message ending the communication is sent at block 1422. If a birth date was provided, then the affirmative response is logged at block 1424. Also, if the patient's response at block 1410 was affirmative the affirmative response is also logged at block 1424. Continuing after the logging of the affirmative response at block 1424 an inquiry loop is initiated at block 1426 which is represented by the method in FIG. 15. Alternatively, at block 1404 if the patient is confirmed a welcome message is sent at block 1428.

Figure 15:
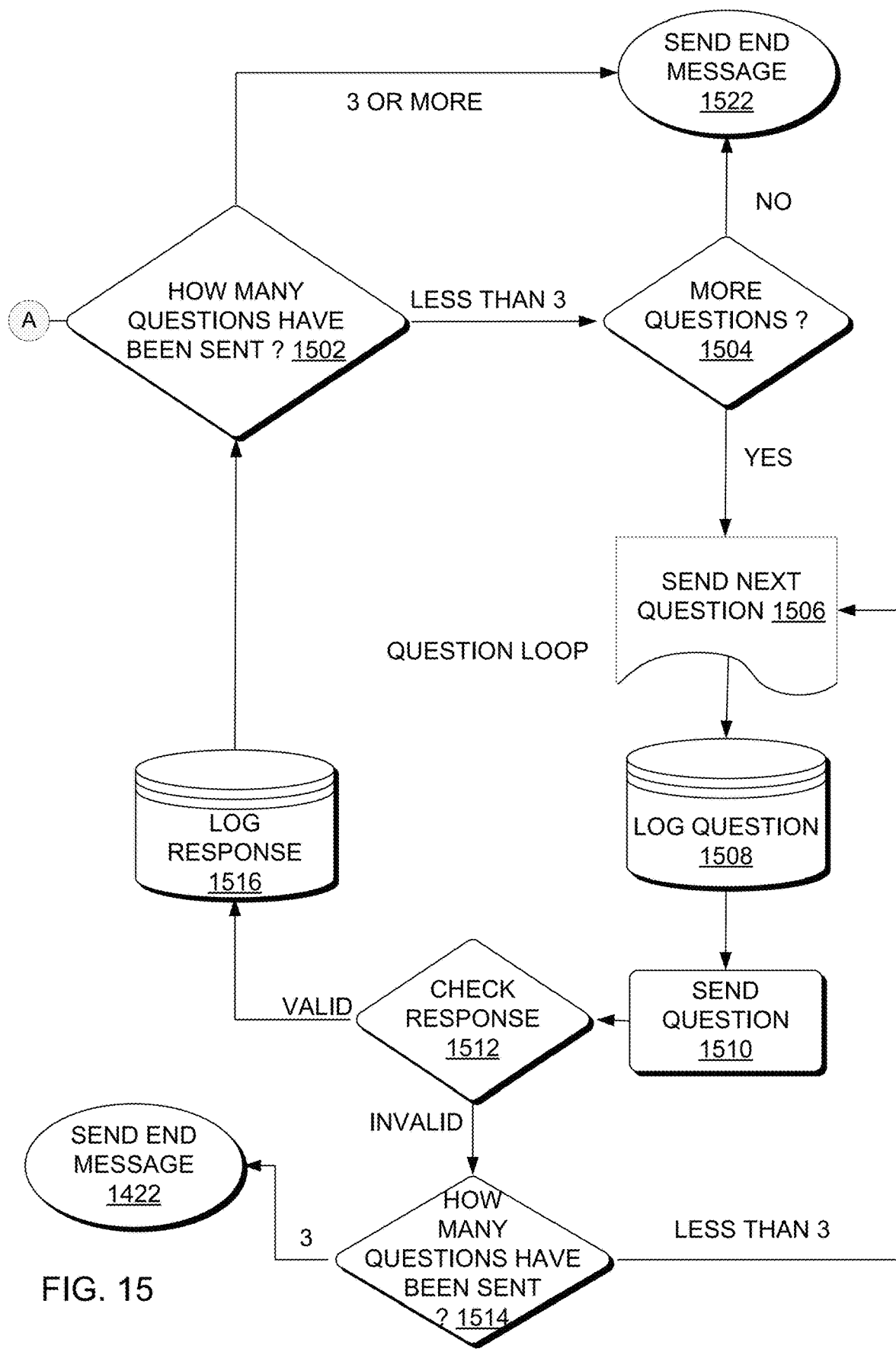
FIG. 15 is a block diagram of a method of inquiry that can be repeated, according to an implementation.

FIG. 15 is a block diagram of a method of inquiry that can be repeated 1500, according to an implementation. Method 1500 starts with determining how many questions have been sent already at block 1502. If three or more messages have been sent already and end message is sent at block 1422. If less than three messages have been sent a determination is made as to whether there are more questions to be sent at block 1504. If no more questions are to be sent. Then an end message is sent at block 1422. If more messages are to be sent then the next message is sent at block 1506, the question is logged at block 1508 and the question is sent at block 1510. A determination is made as to whether or not the response to the question is valid at block 1512 and if the response is invalid then a determination as to how many questions have been sent at block 1514 and if three questions have been sent then an end message is sent at block 1422. If less than three questions have been sent, then the next question is sent at block 1506. If the response is valid at block 1512 then the response is logged at block 1516 and a determination as to how many questions have been sent is made at block 1502.

Figure 16:
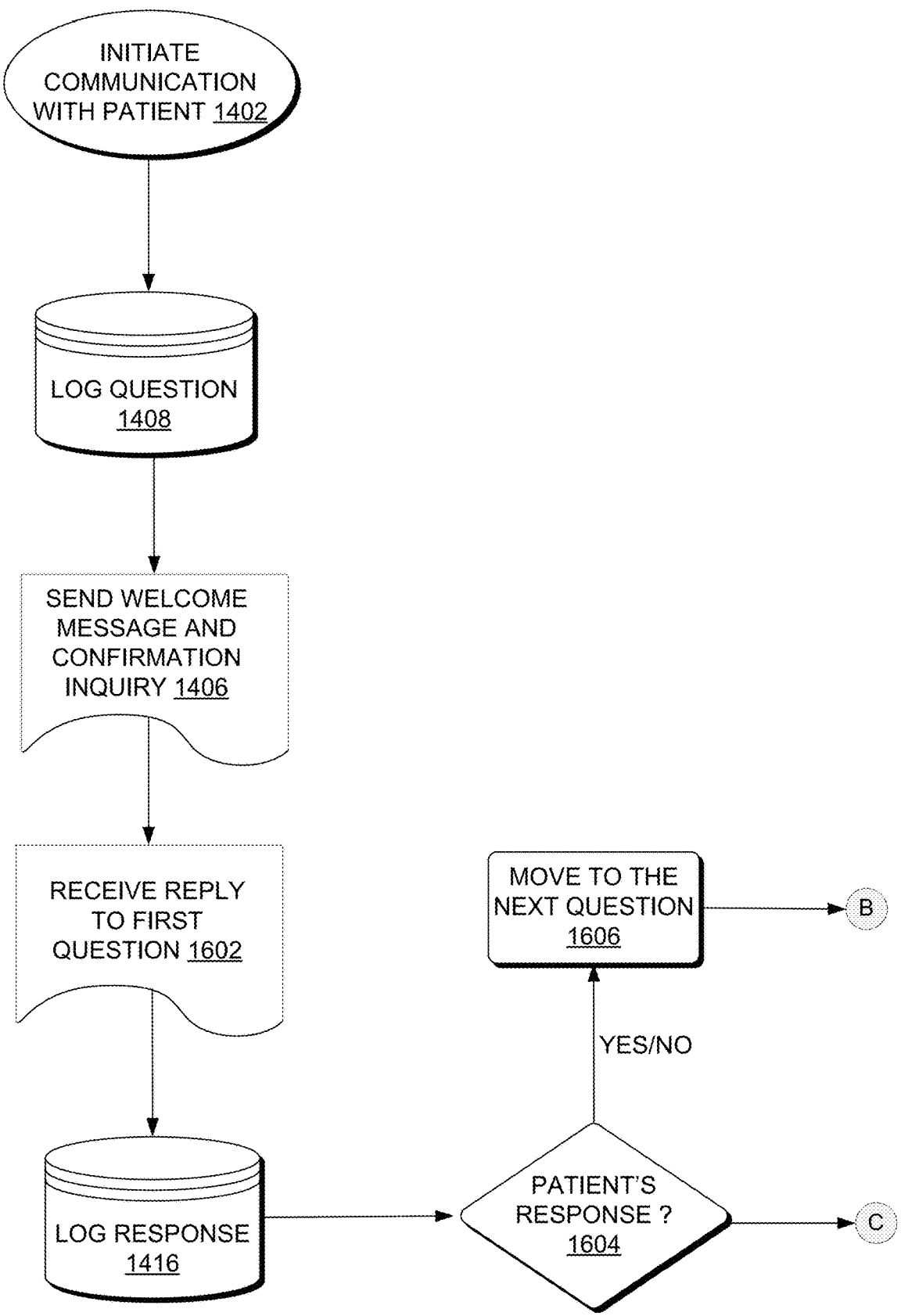
FIG. 16 is a block diagram of a method of inquiry, according to an implementation.

FIG. 16 is a block diagram of a method of inquiry 1600, according to an implementation. Method 1600 includes initiating communication with a patient at block 1402 and then logging a first question at block 1408 and sending a welcome message and Confirmation inquiry at block 1406 and receiving a reply to the first question at block 1602 and logging the response to the first question at block 1516. Thereafter the response is evaluated 1604 to determine if the answer to the first question was "yes" or "no", in which case the next question is advanced at block 1606 and the question loop in FIG. 17 is started otherwise if the patience response is something other than "yes" or "no", the question loop in FIG. 17 is started.

Figure 17:
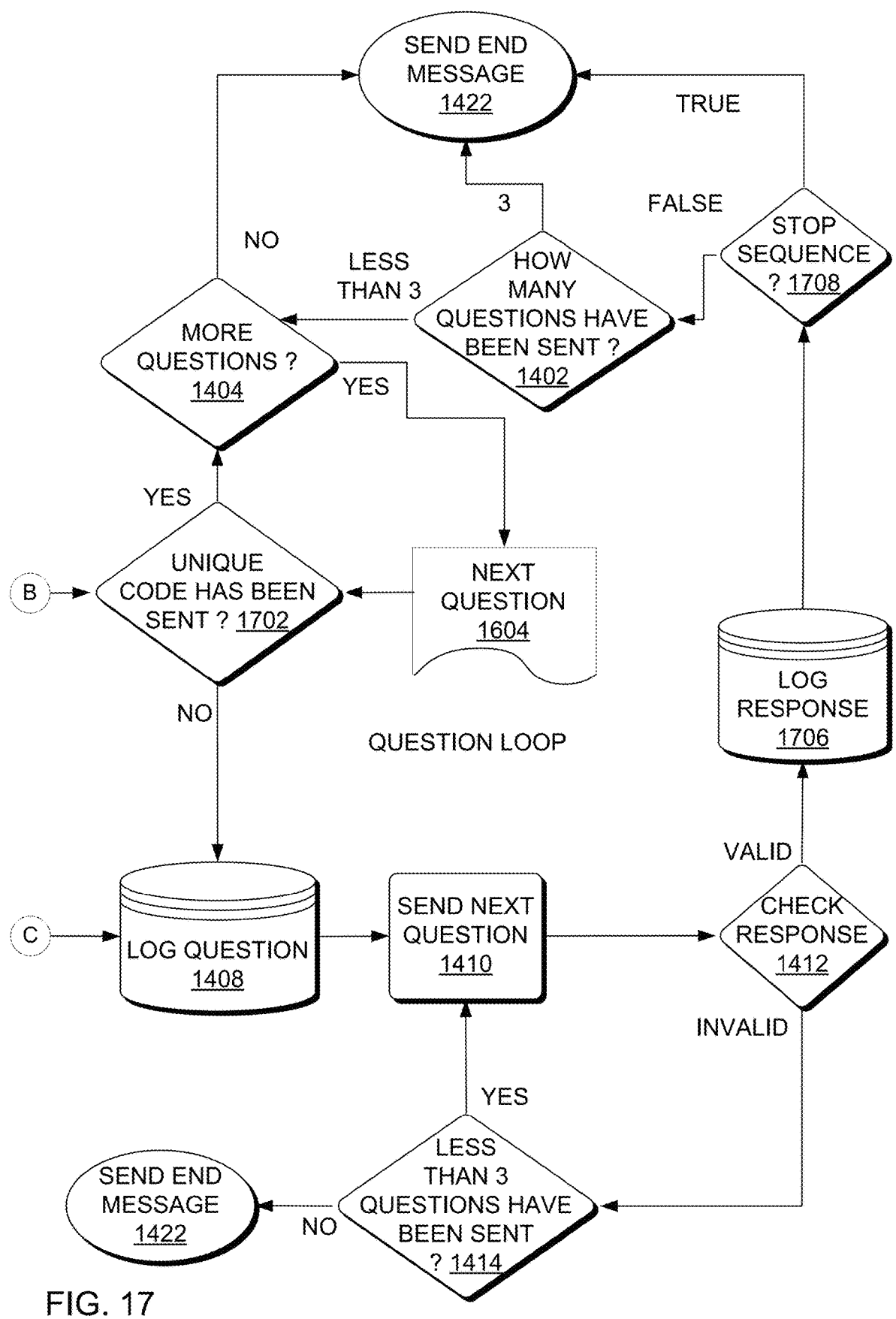
FIG. 17 is a block diagram of a method of inquiry that can be repeated, according to an implementation.

FIG. 17 is a block diagram of a method of inquiry that can be repeated 1700, according to an implementation. When method 1700 is entered through point B, determination is made as to whether a unique code has been sent at block 1702. If a unique code has been sent, then a determination as to whether or not there are more questions to be sent is performed at block 1504. If no more questions are to be sent, then an end message is sent at block 1422. When it is determined at block 1504 that no more questions are to be sent, then the next question is advanced at block 1606 and a determination is made as to whether or not a unique code has been sent at block 1702. When a unique code has not been sent at block 1702 or the method 1700 is entered through point C then a question is logged at block 1508 and the next question is sent at block 1510 and a response to the question is evaluated at block 1512. If the response is invalid, then a determination as to whether or not less than three questions have been sent at block 1514. If less than three questions have not been sent, then an end message is sent at block 1422. If less than three messages have been sent, then the next question is advanced at block 1510. If the response to the question is valid then the response is logged at block 1706 and if a stop sequence exists at block 1708 then an end message is sent at block 1422. If a stop sequence does not exist then a determination as to how many questions have been sent is performed at block 1502 and if three questions have been sent, then an end message is sent at block 1422 but if less than three questions have been sent then a determination as to whether or not more questions exist is performed at block 1502.

CONCLUSION

An architecture of workflow of multimedia objects between heterogeneous computer systems is described that has a technical effect of facilitating the identification of quantitative variances in the multimedia objects. Although specific implementations have been illustrated and described herein, it will be appreciated by those of ordinary skill in the art that any arrangement which is calculated to achieve the same purpose may be substituted for the specific implementations shown. This application is intended to cover any adaptations or variations. For example, although described in procedural terms, one of ordinary skill in the art will appreciate that implementations can be made in an object-oriented design environment or any other design environment that provides the required relationships.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future communication devices, different file systems, and new data types.

The terminology used in this application meant to include all object-oriented, database, graphic document and communication environments and alternate technologies which provide the same functionality as described herein.

The terminology used in this application meant to include all object-oriented, database, graphic document and communication environments and alternate technologies which provide the same functionality as described herein.

The invention claimed is:

1. A computer that is configured to communicate with a server and a smartphone, the computer including:
   a computer-accessible medium to exchange information in a predetermined architecture of interchange of a plurality of device-independent documents between a plurality of heterogeneous computer systems, the computer-accessible medium comprising:
   a data capture module that receives an integrated device-independent document and extracts data from the integrated device-independent document, generating extracted data;
   an external question module that receives the extracted data from the data capture module and generates one or more queries that are encapsulated in a corresponding number of enquiry/inquiry (ENQ) transmissions, the enquiry/inquiry (ENQ) transmissions being short-message-service text messages;
   a communication subsystem that receives the enquiry/inquiry (ENQ) transmissions and that includes an external engagement module that transmits the enquiry/inquiry (ENQ) transmissions to the smartphone that is associated with a customer in the enquiry/inquiry transmissions and receives an acknowledgement transmission or a negative-acknowledgement (NACK) transmission from the smartphone, an acknowledgement/negative-acknowledgement transmission including the acknowledgement transmission or the negative-acknowledgement (NACK) transmission, the acknowledgement/negative-acknowledgement transmission being a short-message-service text message, and the communication subsystem also stores the acknowledgement/negative-acknowledgement transmission in an external interaction database, the external interaction database including a healthcare provider table that has a one-to-many relationship to a superbill table, each entry or record in the healthcare provider table includes fields describing a first name, a last name, a street, a city, a state and a zip code, each entry or record in the superbill table includes an identification, a member identification, a date of service, a patient first name, a patient last name, a patient city, a patient state, a patient zip, a patient social security number, a status (open, closed or expired) and a total amount of charges in the superbill table, the superbill table has a one-to-many relationship to a superbill CPT table, each entry or record in the superbill CPT table has an identification, a superbill identification, a CPT identification, multiplier, and a total amount of charges in the superbill CPT table and a CPT table that has a one-to-many relationship to the a superbill CPT table, wherein the acknowledgement transmission further comprises a single character message indicating acknowledgement of a corresponding enquiry/inquiry transmission, a variance analytic module that includes a server that includes a location specific service component associated with a plurality of healthcare providers that verifies and cross-references active healthcare providers in the extracted data in reference to the healthcare provider table and the superbill table in the external interaction database and that verifies and cross references patient identification in the superbill table and the extracted data, and that retrieves the acknowledgement/negative-acknowledgement transmission from the external interaction database and that generates a quantitative variance from the acknowledgement/negative-acknowledgement transmission, the quantitative variance describing statistical variances and discrepancies within the integrated device-independent document, wherein the quantitative variance is generated by analyzing discrepancies that are at or above a predetermined threshold of a provider that are identified in the extracted data between a CPT code, a performance time of a procedure of the CPT code, a priority code, a sequence code in the acknowledgement/negative-acknowledgement transmission, and from a previous response and between a CPT code, a performance time of a procedure of the CPT code, a priority code, a sequence code in the acknowledgement/negative-acknowledgement transmission in the extracted data, in reference to a response rule table of the external interaction database.

2. The computer of claim 1 further comprising:

wherein a negative-acknowledgement transmission is not implemented, but instead an absence of an acknowledgement transmission from the smartphone is interpreted by the communication subsystem as a negative-acknowledgement transmission, the server configured to control flow of a quantitative variance from the computer to the external interaction database and to manage the smartphone.

* * * * *